United States Patent
Leleti et al.

(10) Patent No.: US 11,951,214 B2
(45) Date of Patent: Apr. 9, 2024

(54) CAPSULE FORMULATIONS

(71) Applicant: CHEMOCENTRYX, INC., San Carlos, CA (US)

(72) Inventors: Manmohan Reddy Leleti, Dublin, CA (US); Jay P. Powers, Pacifica, CA (US)

(73) Assignee: CHEMOCENTRYX, INC., Thousand Oaks, CA (US)

( * ) Notice: Subject to any disclaimer, the term of this patent is extended or adjusted under 35 U.S.C. 154(b) by 0 days.

(21) Appl. No.: 17/545,878

(22) Filed: Dec. 8, 2021

(65) Prior Publication Data

US 2022/0233453 A1 Jul. 28, 2022

Related U.S. Application Data

(63) Continuation of application No. 16/697,523, filed on Nov. 27, 2019, now abandoned.
(Continued)

(51) Int. Cl.
*A61K 9/48* (2006.01)
*A61K 31/4412* (2006.01)

(52) U.S. Cl.
CPC .......... *A61K 9/4858* (2013.01); *A61K 9/4808* (2013.01); *A61K 9/4825* (2013.01); *A61K 9/4833* (2013.01); *A61K 31/4412* (2013.01)

(58) Field of Classification Search
CPC .... A61K 47/44; A61K 9/4808; A61K 9/4833; A61K 47/10; A61K 9/4825; A61K 47/14;
(Continued)

(56) References Cited

U.S. PATENT DOCUMENTS 8,445,515 B2   5/2013   Fan et al.
8,906,938 B2   12/2014  Fan et al.
(Continued)

OTHER PUBLICATIONS

Extended European Search Report dated Jul. 27, 2022 corresponding to EP Application No. 19889873.6 filed Nov. 27, 2019; 4 pages.
(Continued)

*Primary Examiner* — Jianfeng Song
(74) *Attorney, Agent, or Firm* — Mintz Levin Cohn Ferris Glovsky and Popeo PC

(57) ABSTRACT

The present disclosure provides solid solution capsule formulations of Compound 1

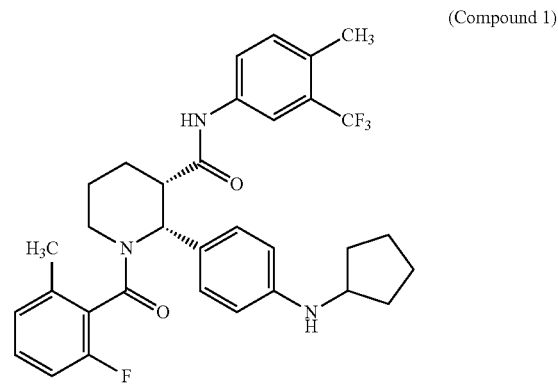

(Compound 1)

and methods of making the same. Also provided herein are methods of treating individuals suffering from or susceptible to a disease or disorder involving pathologic activation of C5a receptors by administering an effective amount of one or more solid solution capsules comprising Compound 1.

(Continued)

Further provided herein are singe unit dosage capsules comprising certain amounts of Compound 1, and kits comprising a solid solution capsule comprising Compound 1.

18 Claims, 9 Drawing Sheets

Related U.S. Application Data

(60) Provisional application No. 62/773,848, filed on Nov. 30, 2018.

(58) Field of Classification Search
CPC ... A61K 31/4412; A61K 9/4858; A61K 47/40
See application file for complete search history.

(56) References Cited

U.S. PATENT DOCUMENTS

| | | |
|---|---|---|
| 9,126,939 B2 | 9/2015 | Fan et al. |
| 9,573,897 B2 | 2/2017 | Fan et al. |
| 9,745,268 B2 | 8/2017 | Fan et al. |
| 10,035,768 B2 | 7/2018 | Fan et al. |
| 10,266,492 B2 | 4/2019 | Fan et al. |
| 10,329,314 B2 | 6/2019 | Fan et al. |
| 10,487,098 B2 | 11/2019 | Fan et al. |
| 10,532,982 B2 | 1/2020 | Fan et al. |
| 11,191,756 B2 | 12/2021 | Deng et al. |
| 11,273,225 B2 | 3/2022 | Guo et al. |
| 11,285,138 B2 | 3/2022 | Bekker |
| 2005/0008697 A1 | 1/2005 | Gorissen |
| 2007/0298099 A1 | 12/2007 | Peresypkin et al. |
| 2010/0311753 A1 | 12/2010 | Fan et al. |
| 2011/0086844 A1* | 4/2011 | Gorissen ............. A61K 9/4858 514/212.07 |
| 2011/0866844 | 4/2011 | Gorissen |
| 2011/0312973 A1* | 12/2011 | Liepold ................. A61P 31/12 514/255.05 |
| 2017/0114017 A1* | 4/2017 | Fan ........................ A61P 9/00 |
| 2017/0246186 A1 | 8/2017 | Giliyar et al. |
| 2018/0179160 A1 | 6/2018 | Fan et al. |
| 2018/0280530 A1 | 10/2018 | Guo et al. |
| 2019/0134020 A1 | 5/2019 | Deng et al. |
| 2019/0144389 A1 | 5/2019 | Fan et al. |
| 2020/0170957 A1 | 6/2020 | Leleti et al. |

OTHER PUBLICATIONS

International Search Report dated Feb. 12, 2020 corresponding to PCT/US2019/063547 filed Nov. 27, 2019; 15 pages.

Bekker, Pirow et al., "Characterization of Pharmacologic and Pharmacokinetic Properties of CCX168, a Potent and Selective Orally Administered Complement 5a Receptor Inhibitor, Based on Preclinical Evaluation and Randomized Phase 1 Clinical Study," *PLOS One* (Oct. 21, 2016); 19 pages.

EU Clinical Trials Register, https://www.clinicaltrialsregister.eu/ctr-search/trial/2017-001821-42/IT "A Randomized, Double-Blind, Placebo-Controlled Phase 2 Study to Evaluate the Safety and Efficacy of Avacopan (CCX168) in Patients with C3 Glomerulopathy," Member State Concerned: Italy—Italian Medicines Agency: EudraCT No. 2017-001821-42; Sponsor's protocol code No. CL01_168; Other identifiers: Name: IND Number; No. 132 321; Trial is part of a Pediatric Investigation Plan; Date on which this record was first entered in the EudraCT database: Nov. 14, 2017; 12 pages.

Healy, Anne Marie et al., "Pharmaceutical solvates hydrates and amorphous forms: A special emphasis on cocrystals," *Advanced Drug Delivery Reviews* (available online Mar. 22, 2017) 117:25-46.

Huang, Yanbin et al., "Fundamental aspects of solid dispersion technology for poorly soluble drugs," *Acta Pharmaceutica Sinica B* (2014; accepted Oct. 15, 2013) 4(1):18-25.

Karolewicz, Bozena et al., "Solid dispersions in pharmaceutical technology. Part I. Classification and methods to obtain solid dispersions," *Polim. Med.* (Jul. 2012) 42(1):17-27.

Handbook of Pharmaceutical Excipients. Sixth edition. Edited by Raymond C. Rowe, Paul J. Sheskey and Marian E. Quinm. *Pharmaceutical Press and American Pharmacists Association*. London, Chicago. 2009; p. 391, 10 Typical properties; pp. 518-519; 10 Typical properties, Melting point.

\* cited by examiner

CAPSULE FORMULATIONS

CROSS-REFERENCES TO RELATED APPLICATIONS

This application is a continuation of U.S. patent application Ser. No. 16/697,523 filed Nov. 27, 2019, which is an application claiming priority benefit under 35 U.S.C. § 119(e) of U.S. Provisional Application No. 62/773,848 filed Nov. 30, 2018, each of which is herein incorporated by reference in its entirety for all purposes.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The complement system plays a central role in the clearance of immune complexes and in immune responses to infectious agents, foreign antigens, virus infected cells and tumor cells. Inappropriate or excessive activation of the complement system can lead to harmful, and even potentially life-threatening consequences due to severe inflammation and resulting tissue destruction. These consequences are clinically manifested in various disorders including septic shock; myocardial, as well as, intestinal ischemia/reperfusion injury; graft rejection; organ failure; nephritis; pathological inflammation; and autoimmune diseases.

The complement system is composed of a group of proteins that are normally present in the serum in an inactive state. Activation of the complement system encompasses mainly three distinct pathways, i.e., the classical, the alternative, and the lectin pathway (V. M. Holers, *In Clinical Immunology: Principles and Practice*, ed. R. R. Rich, Mosby Press; 1996, 363-391): 1) The classical pathway is a calcium/magnesium-dependent cascade, which is normally activated by the formation of antigen-antibody complexes. It can also be activated in an antibody-independent manner by the binding of C-reactive protein, complexed with ligand, and by many pathogens including gram-negative bacteria. 2) The alternative pathway is a magnesium-dependent cascade which is activated by deposition and activation of C3 on certain susceptible surfaces (e.g. cell wall polysaccharides of yeast and bacteria, and certain biopolymer materials). 3) The lectin pathway involves the initial binding of mannose-binding lectin and the subsequent activation of C2 and C4, which are common to the classical pathway (Matsushita, M. et al., *J. Exp. Med.* 176: 1497-1502 (1992); Suankratay, C. et al., *J. Immunol.* 160: 3006-3013 (1998)).

The activation of the complement pathway generates biologically active fragments of complement proteins, e.g. C3a, C4a and C5a anaphylatoxins and C5b-9 membrane attack complexes (MAC), all which mediate inflammatory responses by affecting leukocyte chemotaxis; activating macrophages, neutrophils, platelets, mast cells and endothelial cells; and increasing vascular permeability, cytolysis and tissue injury.

Complement C5a is one of the most potent proinflammatory mediators of the complement system. (The anaphylactic C5a peptide is 100 times more potent, on a molar basis, in eliciting inflammatory responses than C3a.) C5a is the activated form of C5 (190 kD, molecular weight). C5a is present in human serum at approximately 80 µg/ml (Kohler, P. F. et al., *J. Immunol.* 99: 1211-1216 (1967)). It is composed of two polypeptide chains, α and β, with approximate molecular weights of 115 kD and 75 kD, respectively (Tack, B. F. et al., *Biochemistry* 18: 1490-1497 (1979)). Biosynthesized as a single-chain promolecule, C5 is enzymatically cleaved into a two-chain structure during processing and secretion. After cleavage, the two chains are held together by at least one disulphide bond as well as noncovalent interactions (Ooi, Y. M. et al., *J. Immunol.* 124: 2494-2498 (1980)).

Recent work has identified Compound 1

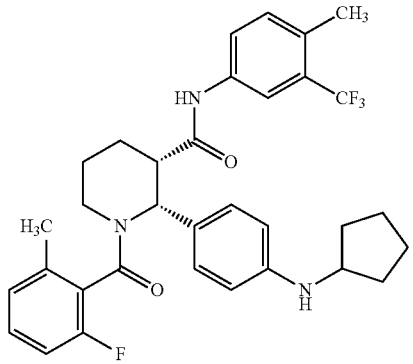 [SMILES: Cc1ccc(NC(=O)[C@H]2CCCN(C(=O)c3c(C)cccc3F)[C@H]2c2ccc(NC3CCCC3)cc2)cc1C(F)(F)F]

as useful for treating C5a mediated diseases. Compound 1 is classed as a compound belonging to Class II of the Biopharmaceutics Classification System (BCS) having poor solubility in the aqueous environment of the gastrointestinal (GI) tract but high permeability across membranes. Thus, its resorption is controlled by its solubility and rate of dissolution in the GI tract. Despite the disclosure of this compound, a pharmaceutical formulation that provides manufacturability, consistent stability, bioavailability, and pharmacokinetics has not been developed.

As such, there exists a need to produce pharmaceutical formulations that meet the necessary manufacturability, stability, bioavailability, and pharmacokinetic requirements to make them suitable for oral administration to humans or other animals. The present disclosure addresses these needs and provides related advantages as well.

BRIEF SUMMARY

In one aspect, provided herein is a solid solution capsule comprising Compound 1 as a free base, in its neutral form or in the form of a pharmaceutically acceptable salt

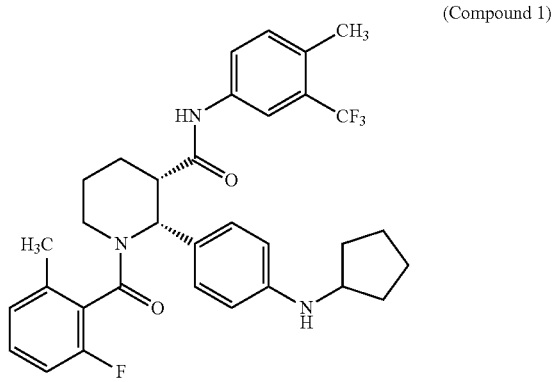 [SMILES: Cc1ccc(NC(=O)[C@H]2CCCN(C(=O)c3c(C)cccc3F)[C@H]2c2ccc(NC3CCCC3)cc2)cc1C(F)(F)F]

(Compound 1)

and a vehicle comprising
- at least one non-ionic surfactant having a hydrophilic-lipophilic balance (HLB) value of at least 10, and
- at least one water-soluble solubilizer having a melting point at or above 37° C.

In one aspect, provided herein is a method of preparing a solid solution capsule comprising Compound 1 a free base, in its neutral form or in the form of a pharmaceutically acceptable salt

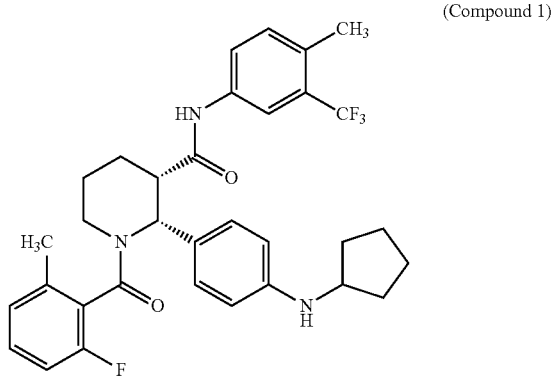 [SMILES: Cc1ccc(NC(=O)[C@H]2CCCN(C(=O)c3c(C)cccc3F)[C@H]2c2ccc(NC3CCCC3)cc2)cc1C(F)(F)F]

(Compound 1)

and a vehicle comprising
- at least one non-ionic surfactant has a hydrophilic-lipophilic balance (HLB) value of at least 10, and
- at least one water-soluble solubilizer having a melting point at or above 37° C.;

said method comprising
(a) melting the vehicle;
(b) combining the melted vehicle obtained in step (a) with Compound 1 to form a drug solution;
(c) encapsulating the drug solution; and
(d) cooling the encapsulated drug solution to form a solid solution capsule comprising Compound 1.

In one aspect, provided herein is a solid solution capsule comprising Compound 1 as a free base, in its neutral form or in the form of a pharmaceutically acceptable salt

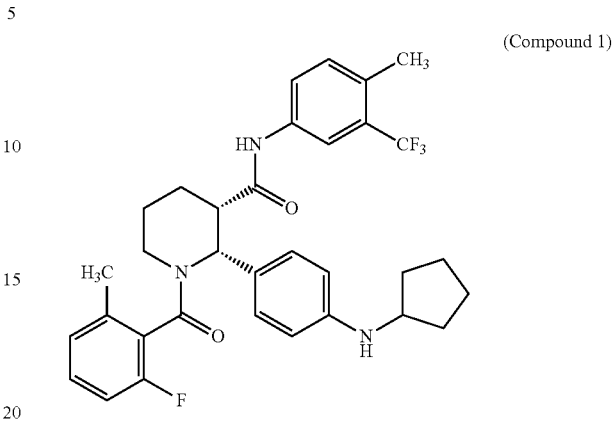

(Compound 1)

and a vehicle comprising
- at least one non-ionic surfactant having a hydrophilic-lipophilic balance (HLB) value of at least 10, and
- at least one water-soluble solubilizer having a melting point at or above 37° C., said solid solution capsule prepared according to the methods described herein.

In one aspect, provided herein are methods of treating an individual suffering from or susceptible to a disease or disorder involving pathologic activation of C5a receptors, comprising administering to the individual an effective amount of one or more solid solution capsule comprising Compound 1 as described herein.

In one aspect, provided herein is a single unit dosage capsule comprising about 2.6 mg to 25.2 mg of Compound 1 as a free base, in its neutral form

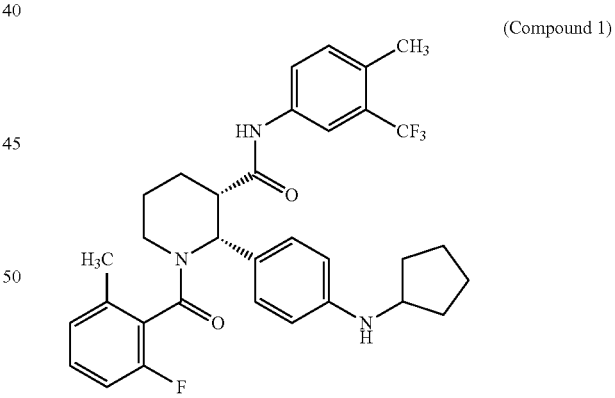

(Compound 1)

and a vehicle comprising
- at least one non-ionic surfactant has a hydrophilic-lipophilic balance (HLB) value of at least 10, and
- at least one water-soluble solubilizer having a melting point at or above 37° C.

In one aspect, provided herein are kits comprising a solid solution capsule comprising Compound 1 as described herein.

Other objects, features, and advantages of the present invention will be apparent to one of skill in the art from the following detailed description and figures.

DETAILED DESCRIPTION OF THE INVENTION

I. General

Figure 1:
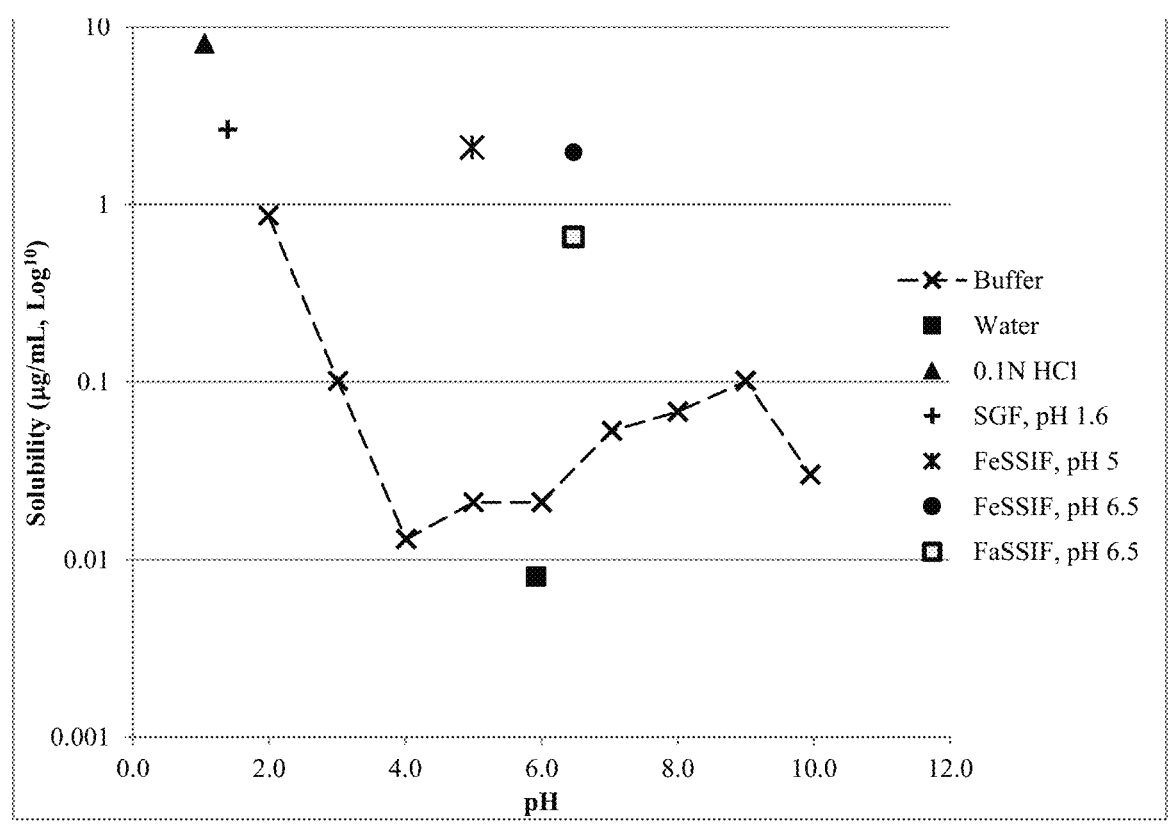
FIG. 1 plots the solubility profile of Compound 1 as a free base at various pH values.

Compound 1 has been found to possess extremely poor solubility across a broad pH range. Additionally, Compound 1 lacked solubility in a number of excipients tested. Compound 1 has been successfully formulated as a liquid; however, such formulations included ethanol. Ethanol readily evaporates during both dose preparation and storage, thereby introducing dosing inaccuracies and, at times, causing Compound 1 to crash out of solution. In order to overcome the difficulties in formulating Compound 1 for pharmaceutical uses, the present disclosure provides a solid solution capsule formulation of Compound 1 and methods of making the same.

The solid solution capsules described herein provide Compound 1 completely and molecularly dissolved in a matrix, dispersed in a matrix, or a mixture thereof. That is, the drug product is a solid solution of drug substance in the amorphous capsule fill matrix. In some embodiments, dissolution of Compound 1 in the matrix can be determined through visual inspection of the capsule fill matrix. Thus, completely and molecularly dissolved Compound 1 can include a solid solution capsule fill matrix that does not have observable clusters of undissolved Compound 1 and appears as a uniform solid solution to the naked eye.

Advantageously, the solid solution capsule formulations described herein avoids or reduces crystallization of the drug substance in the molecularly dissolved or dispersed matrix and provides excellent stability, bioavailability, and pharmacokinetic properties. A key feature of the formulations described herein is the ratio of the at least one non-ionic surfactant having a HLB value of at least 10 and the at least one water-soluble solubilizer having a melting point at or above 37° C. that provide a useful pharmaceutical composition.

II. Definitions

The term "treating" or "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms).

The term "pharmaceutically acceptable salts" is meant to include salts of the active compounds which are prepared with relatively nontoxic acids or bases, Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19 or P. Heinrich, Stahl, Camille G. Wemouth, Handbook of Pharmaceutical Salts, 2002. Wiley-VCH).

The neutral form of Compound 1 may be regenerated by contacting the salt with a base or acid and isolating the parent compound in the conventional manner. The parent form of Compound 1 differs from the various salt forms in certain physical properties, such as solubility in polar solvents, but otherwise the salts are equivalent to the parent form of Compound 1 for the purposes of the present disclosure.

"Solid solution capsule" refers to a formulation comprising the drug substance dissolved or dispersed in an excipient matrix that is encapsulated. The drug substance is completely and molecularly dissolved or dispersed in the excipient matrix, or a mixture thereof. In the present invention, the drug substance, i.e. Compound 1 as a free base, in its neutral form or in the form of a pharmaceutically acceptable salt, is dissolved or dispersed in an excipient matrix, which is a vehicle comprising at least one non-ionic surfactant having a hydrophilic-lipophilic balance (HLB) value of at least 10 and at least one water-soluble solubilizer having a melting point at or above 37° C.

"Nonionic surfactant" refers to a surfactant in which the hydrophilic portion of the surfactant carries no charge. Two non-limiting classes of nonionic surfactants useful in the present disclosure are (a) polyoxyethylene castor oil derivatives, and (b) polyoxyethylene derivatives of a fatty acids containing from about 8 to about 22 carbon atoms. The carbon atoms of the fatty acid can include one or more points of unsaturation or one or more points of substitution (e.g. ricinoleic acid).

The term "hydrophilic-lipophilic balance" ("HLB") is a relative measure of the ratio of polar and non-polar groups present in a surfactant. In some embodiments, the HLB value is calculated by the Griffin method using the formula:

$$HLB=20*Mh/M$$

where Mh is the molecular mass of the hydrophilic portion of the molecule, and M is the molecular mass of the whole molecule, giving a result on a scale of 0 to 20. An HLB value of 0 corresponds to a completely lipophilic/hydrophobic molecule, and a value of 20 corresponds to a completely hydrophilic/lipophobic molecule. Further details of Griffin's method can be found in Griffin (Journal of the Society of Cosmetic Chemists 1949 1: 311-326) and Griffin (Journal of the Society of Cosmetic Chemists 1954 5: 249-256) which are incorporated herein by reference for all purposes. In some embodiments, the HLB value is calculated by the Davies method when is described in Davies J. T., "A Quantitative Kinetic Theory of Emulsion Type, I. Physical Chemistry of the Emulsifying Agent," Gas/Liquid and Liquid/Liquid Interface. *Proceedings the International Congress of Surface Activity* 426-438 (1957) which is incorporated herein by reference for all purposes. In some embodiments, when determining the HLB values of compositions where the hydrophilic portions consists of ethylene oxide only, the HLB value is calculated using the formula $$HLB=E/5$$

where E is the weight percent of the oxyethylene content. Further information for this calculation is described in "The HLB system: a time-saving guide to emulsifier selection. Wilmington. ICI Americas, Inc. 1984. Print, the contents of which is incorporated herein by reference for all purposes.

"Water-soluble solubilizer" refers to compositions that that are readily molecularly soluble in water at neutral pH and ambient temperature. For example, water-soluble solubilizers have a solubility in water of at least 15, 20, 35, 30, 35, 40, 45 or 50 g/L at 25° C. In some embodiments, water-soluble solubilizers have a solubility in water of at least 40 g/L at 25° C. Typical water-soluble solubizers having a melting point at or above 37° C. are polyethylene glycols having an average molecular weight of 1000 to 6000. Additional water-soluble solubilizers having a melting point at or above 37° C. also include poloxamers such as poloxamer 188, poloxamer 237, poloxamer 338 and poloxamer 407.

The "total fill weight" refers to the amount of material that is encapsulated within a capsule shell as described herein. The "total fill weight" does not include the weight of the capsule itself nor any other additives used to seal the capsule.

"Compound 1" is a chemical compound having an IUPAC name of (2R,3 S)-2-(4-(cyclopentylamino)phenyl)-1-(2-fluoro-6-methylbenzoyl)-N-(4-methyl-3-(trifluoromethyl) phenyl)piperidine-3-carboxamide, and the structure shown below:

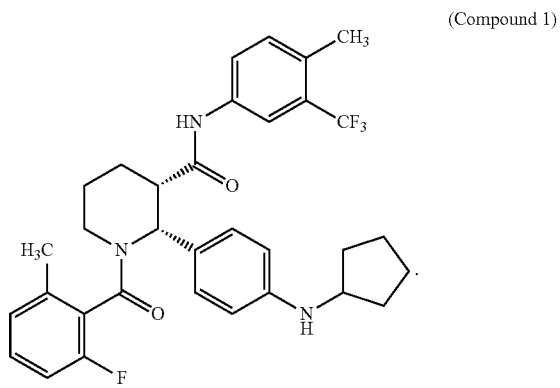 [SMILES: Cc1ccc(NC(=O)[C@H]2CCCN(C(=O)c3c(C)cccc3F)[C@H]2c2ccc(NC3CCCC3)cc2)cc1C(F)(F)F]

(Compound 1)

As used herein, a condition is considered "responsive to C5a receptor modulation" if modulation of C5a receptor activity results in the reduction of inappropriate activity of a C5a receptor.

The term "individual" refers to mammals, which includes primates (especially humans), domesticated companion animals (such as dogs, cats, horses, and the like) and livestock (such as cattle, pigs, sheep, and the like), with dosages as described herein. In some embodiments, the term "individual" refers to a human.

III. Detailed Description of Embodiments

A. Solid Solution Capsule

In some aspects, provided herein are solid solution capsule formulations comprising Compound 1 as a free base, in its neutral form or in the form of a pharmaceutically acceptable salt

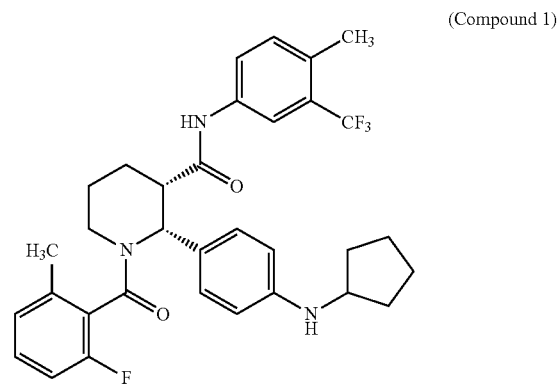 [SMILES: Cc1ccc(NC(=O)[C@H]2CCCN(C(=O)c3c(C)cccc3F)[C@H]2c2ccc(NC3CCCC3)cc2)cc1C(F)(F)F]

(Compound 1)

and a vehicle comprising
- at least one non-ionic surfactant has a hydrophilic-lipophilic balance (HLB) value of at least 10, and
- at least one water-soluble solubilizer having a melting point at or above 37° C.

Typically, suitable non-ionic surfactants having an HLB value of at least 10 include (a) polyoxyethylene castor oil derivatives, and (b) polyoxyethylene derivatives of polyol esters, wherein the polyoxyethylene derivative of polyol ester is derived from a fatty acid containing from about 8 to about 22 carbon atoms. The carbon atoms of the fatty acid can include one or more points of unsaturation or one or more points of substitution (e.g. ricinoleic acid).

In some embodiments, suitable non-ionic surfactants having an HLB value of at least 10 are macrogol-glycerol hydroxystearate polymers such as polyoxyethylene 40 castor oil, polyoxyethylene 40 hydrogenated castor oil (also known as macrogol-40-glycerol hydroxystearate, it previous tradename Cremophor® RH40, and its current tradename Kolliphor® RH40), macrogolglycerol ricinoleate (also known as polyethoxxethylene 35 castor oil, by its previous tradename Cremophor® EL, and by its current tradename Kolliphor® EL), macrogol-15-hydroxystearate (also known by its previous tradename Solutol® HS 15 and its current tradename Kolliphor HS15), polyoxyethylene 60 castor oil, polyoxyethylene 60 hydrogenator castor oil, polyoxyethylene 100 hydrogenated castor oil, polyoxyethylene 200 castor oil, polyoxyethylene 200 hydrogenated castor oil.

Suitable water-soluble solubilizers having a melting point at or above 37° C. can be polyethylene glycols (PEGs) having a minimum average molecular weight of 1000 and a maximum average molecular weight of 20,000. Typical polyethylene glycols used as solubilizers in the present invention are PEG-1000, PEG-1500, PEG-1540, PEG-2000, PEG-3000, PEG-3350, PEG-4000, PEG-6000, PEG-8000, PEG-10000, and PEG-20000. In some embodiments, the at least one water-soluble solubilizer is PEG-3000, PEG-3350, PEG-4000, PEG-6000. In some embodiments, the at least one water-soluble solubilizer is PEG-4000.

Also suitable as water-soluble solubilizers having a melting point at or above 37° C. are solid poloxamers, also known as poloxamer polyols with average molecular weights between 6000 and 18000 or by their tradename Pluronics®, which have the formula $HO(C_2H_4O)_a(C_3H_6O)_b(C_2H_4O)_aH$. Examples of suitable poloxamers are poloxamer 188, poloxamer 237, poloxamer 338 and poloxamer 407.

In certain embodiments, the at least one non-ionic surfactant having a hydrophilic-liphophilic balance (HLB) value of at least 10 and the at least one water-soluble solubilizer having a melting point at or above 37° C. is a single component. Such a component includes a hydrophilic polyethylene glycol (PEG) chain attached to a lipophilic fatty acid or fatty alcohol component (e.g. a macrogolglycerol hydroxystearate). The longer the PEG chain length, i.e. the higher the HLB value, the more likely it is that dissociation between the PEG chain and the lipophilic component occurs. Such single component vehicles provide a non-ionic surfactant having an HLB value of at least 10 and free PEG polymer chains acting as water-soluble solubilizers.

Without wishing to be bound by any particular theory, it is thought that a capsule formulation comprising a non-ionic surfactant having an HLB value of at least 10 and a water-soluble solubilizer having a melting point at or above 37° C. provides a so-called self-emulsifying or self-solubilizing system. Upon oral administration, the capsule shell dissolves in the gastrointestinal tract followed by dissolution of the solubilizing agent in the gastric fluid with simultaneous formation of micelles comprising molecularly dissolved Compound 1. Thus, a microemulsion or a nanoemulsion is formed that permits Compound 1 to remain in solution despite being surrounded by gastric fluid having a pH value of 3 or above, at which pH value Compound 1 is normally insoluble.

In some embodiments, the solid solution capsule formulations comprising Compound 1 as a free base, in its neutral form or in the form of a pharmaceutically acceptable salt, and a vehicle, said vehicle comprising macrogol-40-glycerol hydroxystearate and PEG-4000.

In some embodiments, the vehicle comprises about 97 to 99% by weight of the total fill weight of said solid solution capsule. In some embodiments, the vehicle comprises about 98% by weight of the total fill weight of said solid solution capsule.

In some embodiments, the solid solution capsule comprises about 1 to 3% of Compound 1 by weight of the total fill weight of said solid solution capsule. In some embodiments, the solid solution capsule comprises about 1 to 2.8% of Compound 1 by weight of the total fill weight of said solid solution capsule. In some embodiments, the solid solution capsule comprises about 2% of Compound 1 by weight of the total fill weight of said solid solution capsule.

In some embodiments, the total weight of the vehicle comprises a 30:70 to 65:35 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is from 30:70 and 65:35. In some embodiments, the total weight of the vehicle comprises a 35:65 to 65:35 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is from 35:65 to 65:35. In some embodiments, the total weight of the vehicle comprises a 45:55 to 55:45 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is from 45:55 to 55:45. In some embodiments, the total weight of the vehicle comprises about a 50:50 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is 50:50. In some embodiments, the total weight of the vehicle comprises about a 40:60 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is 40:60. In some embodiments, the total weight of the vehicle comprises about a 30:70 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is 30:70.

In some embodiments, the total fill weight of said solid solution capsule is about 100 mg to about 1,000 mg. In some embodiments, the total fill weight of said solid solution capsule is about 130 mg to about 900 mg. In some embodiments, the total fill weight of said solid solution capsule is about 250 mg to about 750 mg. In some embodiments, the total fill weight of said solid solution capsule is about 500 mg.

In some embodiments, the solid solution capsule does not include ethanol.

In some embodiments, the solid solution capsule is in a capsule of size #00, #0, #1, #2, #3, #4, or #5. In some embodiments, the solid solution capsule is in a capsule of size #00. In some embodiments, the solid solution capsule is in a capsule of size #0. In some embodiments, the solid solution capsule is in a capsule of size #1.

In some embodiments, the capsule is a hard capsule. In some embodiments, the capsule is a soft capsule.

Capsules of the present disclosure can be sealed using known techniques in the art. For example, a gelatin sealing band comprising a plasticizer such as polysorbate 80 can be used to seal the capsules disclosed herein.

B. Method of Making a Solid Solution Capsule

Also provided herein are methods for making solid solution capsules comprising Compound 1 as a free base, in its neutral form or in the form of a pharmaceutically acceptable salt. The solid solution capsule formulations described herein are manufactured by filling hard shell capsules with warmed drug solution. After filling the warmed drug solution into the capsules, the solution solidifies and forms an amorphous matrix.

In some aspects, provided herein are methods of preparing a solid solution capsule comprising Compound 1 as a free base, in its neutral form or in the form of a pharmaceutically acceptable salt

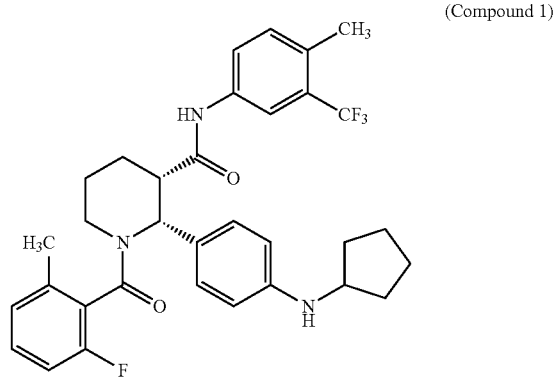 [SMILES: Cc1ccc(NC(=O)[C@H]2CCCN(C(=O)c3c(C)cccc3F)[C@H]2c2ccc(NC3CCCC3)cc2)cc1C(F)(F)F]

(Compound 1)

and a vehicle comprising
  at least one non-ionic surfactant having a hydrophilic-lipophilic balance (HLB) value of at least 10, and
  at least one water-soluble solubilizer having a melting point at or above 37° C.;
said method comprising
  (a) melting the vehicle;
  (b) combining the melted vehicle obtained in step (a) with Compound 1 to form a drug solution;
  (c) encapsulating the drug solution in a capsule shell; and
  (d) cooling the encapsulated drug solution to form a solid solution capsule comprising Compound 1.

Melting the vehicle is achieved using standard techniques in the art. The temperature for melting will depend on the identity of the vehicle. Typical melting techniques include direct heating oven and jacketed mixing tanks. In some embodiments, the vehicle in step (a) is heated to about 40, 45, 50, 55, 60, 65, 70, 75, 80, 85, 90 or more degrees C. In some embodiments, the vehicle in step (a) is heated to about 50° to 85° C. In some embodiments, the vehicle in step (a) is heated to about 50° C. In some embodiments, the vehicle in step (a) is heated to about 60° C. In some embodiments, the vehicle in step (a) is heated to about 70° C. In some embodiments, the vehicle in step (a) is heated to about 80° C.

In some embodiments, step (a) comprises
  (i) heating at least one non-ionic surfactant having an HLB value of at least 10 to form a melted surfactant;
  (ii) heating at least one water-soluble solubilizer to form a melted solubilizer; and
  (iii) combining melted solubilizer with melted surfactant to form a melted vehicle.

As described above, the melting of step (a) can be performed using standard heating techniques in the art. This also applies to steps (i) and (ii). In some embodiments, the heating temperatures of steps (i) and (ii) are the same. In some embodiments, the heating temperatures of steps (i) and (ii) are different.

In some embodiments, the at least one non-ionic surfactant having an HLB value of at least 10 in step (i) is heated to about 40, 45, 50, 55, 60, 65, 70, 75, 80, 85, 90 or more degrees C. In some embodiments, the at least one non-ionic surfactant having an HLB value of at least 10 in step (i) is heated to about 50° to 85° C. In some embodiments, the at least one non-ionic surfactant having an HLB value of at least 10 in step (i) is heated to about 50° to 70° C. In some embodiments, the at least one non-ionic surfactant having an HLB value of at least 10 in step (i) is heated to about 50° C. In some embodiments, the at least one non-ionic surfactant having an HLB value of at least 10 in step (i) is heated to about 60° C. In some embodiments, the at least one non-ionic surfactant having an HLB value of at least 10 in step (i) is heated to about 70° C. In some embodiments, the at least one non-ionic surfactant having an HLB value of at least 10 in step (i) is heated to about 80° C.

In some embodiments, the at least one water-soluble solubilizer in step (ii) is heated to about 40, 45, 50, 55, 60, 65, 70, 75, 80, 85, 90 or more degrees C. In some embodiments, the at least one water-soluble solubilizer in step (ii) is heated to about 50° to 90° C. In some embodiments, the at least one water-soluble solubilizer in step (ii) is heated to about 80° to 85° C. In some embodiments, the at least one water-soluble solubilizer in step (ii) is heated to about 50° C. In some embodiments, the at least one water-soluble solubilizer in step (ii) is heated to about 60° C. In some embodiments, the at least one water-soluble solubilizer in step (ii) is heated to about 70° C. In some embodiments, the at least one water-soluble solubilizer in step (ii) is heated to about 80° C.

In some embodiments, the at least one non-ionic surfactant having an HLB value of at least 10 in step (i) is heated to about 50 to 70° C., and the at least one water-soluble solubilizer in step (ii) is heated to about 80 to 85° C. In some embodiments, the at least one non-ionic surfactant having an HLB value of at least 10 in step (i) is heated to about 60° C., and the at least one water-soluble solubilizer in step (ii) is heated to about 80° C.

After performing steps (i) and (ii), the melted solubilizer may have the temperature adjusted to a temperature within the tolerances of the capsule shell. For example, the temperature tolerance of a gelatin capsule shell is about 65° C. Difference capsule shells can tolerate different temperatures, a person of skill in the art would readily identify appropriate temperatures based on the capsule shell being used.

When contacting the melted solubilizer and the melted surfactant, agitation is generally applied to ensure mixing of the melted surfactant and melted solubilizer. Typically, stirring is employed. The time of agitation/stirring will vary depending on the components of the melted surfactant and melted solubilizer, the size of the preparation, and the heating temperatures used. In some embodiments, stirring is performed for 0.25, 0.5, 0.75, 1, 2 or more hours. Agitation may be performed under vacuum during this step to dearate the solution.

Returning to step (b), when contacting the melted vehicle with Compound 1 in step (b), the drug is dissolved in the heated vehicle. Dissolution of Compound 1 can be achieved by a number of techniques including waiting an appropriate amount of time or agitating the solution to increase the rate of dissolution. In some embodiments, the heated vehicle with Compound 1 in step (b) is agitated by stirring. Stirring times can be between one to six or more hours. In some embodiments, the stirring time is for 1, 2, 3, 4, 5 6 or more hours. In some embodiments, the stirring time is for about 3.5 hours.

Encapsulation of the drug solution is performed using known techniques in the art. One such machine useful for encapsulating is a Shionogi F40 filler. A person of skill in the art will be aware of additional equivalent machines.

There are a number of means known in the art for cooling a desired substance. The cooling in recited step (d) can include passive activities such as allowing the encapsulated drug solution to equilibrate to room temperature or more active steps such as placing the encapsulated drug solution in a refrigerated area to increase the rate of cooling.

A person of skill in the art will recognize the each of the above steps does not need to be performed in the recited order to prepare a solid solution capsule comprising Compound 1. For example, after dissolution of Compound 1 in the heated vehicle (step (b)), to form a drug mixture, the drug mixture can be cooled to form a solid solution. As discussed above, cooling can include passive activities such as allowing the encapsulated drug solution to equilibrate to room temperature or more active steps such as placing the encapsulated drug solution in a refrigerated area to increase the rate of cooling.

In some embodiments, the total weight of the vehicle comprises a 30:70 to 65:35 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is from 30:70 and 65:35. In some embodiments, wherein the total weight of the vehicle comprises a 35:65 to 65:35 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is from 35:65 to 65:35. In some embodiments, the total weight of the vehicle comprises a 45:55 to 55:45 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is from 45:55 to 55:45. In some embodiments, the total weight of the vehicle comprises about a 50:50 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is 50:50. In some embodiments, the total weight of the vehicle comprises about a 40:60 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is 40:60. In some embodiments, the total weight of the vehicle comprises about a 30:70 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is 30:70.

As described in the preceding paragraphs, these methods are used to prepare a solid solution capsule. Accordingly, in some aspects, also provided herein is a solid solution capsule comprising Compound 1 prepared according to the methods describe herein.

In some embodiments, provided herein is a solid solution capsule comprising Compound 1 as a free base, in its neutral form or in the form of a pharmaceutically acceptable salt

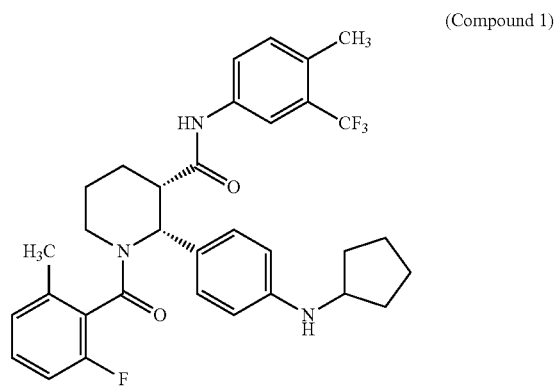 [SMILES: Cc1ccc(NC(=O)[C@H]2CCCN(C(=O)c3c(C)cccc3F)[C@H]2c2ccc(NC3CCCC3)cc2)cc1C(F)(F)F]

(Compound 1)

and a vehicle comprising
- at least one non-ionic surfactant having a hydrophilic-lipophilic balance (HLB) value of at least 10, and
- at least one water-soluble solubilizer having a melting point at or above 37° C.; obtainable by a process comprising
  - (a) melting the vehicle;
  - (b) combining the melted vehicle obtained in step (a) with Compound 1 to form a drug solution;
  - (c) encapsulating the drug solution in a capsule shell; and
  - (d) cooling the encapsulated drug solution to form a solid solution capsule comprising Compound 1.

C. Methods of Treatment

Also provided herein are methods of treating individuals suffering from conditions that are responsive to C5a receptor modulation.

In some aspects provided herein are methods of treating an individual suffering from or susceptible to a disease or disorder involving pathologic activation of C5a receptors, comprising administering to the individual an effective amount of a solid solution capsule comprising Compound 1 as described herein.

In some embodiments, the solid solution capsules comprising Compound 1 described herein are used for treating patients suffering from conditions that are responsive to C5a receptor modulation.

Conditions that can be Treated by C5a Modulation:

Autoimmune disorders—e.g., Rheumatoid arthritis, systemic lupus erythematosus, Guillain-Barre syndrome, pancreatitis, C3 glomerulopathy (C3G), hidradenitis suppurativa (HS), lupus nephritis, lupus glomerulonephritis, immunoglobulin A (IgA) nephropathy, psoriasis, Crohn's disease, vasculitis, irritable bowel syndrome, dermatomyositis, multiple sclerosis, bronchial asthma, pemphigus, pemphigoid, scleroderma, myasthenia gravis, autoimmune hemolytic and thrombocytopenic states, Goodpasture's syndrome (and associated glomerulonephritis and pulmonary hemorrhage), immunovasculitis, tissue graft rejection, hyperacute rejection of transplanted organs; and the like.

Inflammatory disorders and related conditions—e.g., Neutropenia, sepsis, septic shock, Alzheimer's disease, multiple sclerosis, stroke, inflammatory bowel disease (IBD), age-related macular degeneration (AMD, both wet and dry forms), inflammation associated with severe burns, lung injury, and ischemia-reperfusion injury, osteoarthritis, as well as acute (adult) respiratory distress syndrome (ARDS), chronic pulmonary obstructive disorder (COPD), systemic inflammatory response syndrome (SIRS), atopic dermatitis, psoriasis, chronic urticaria and multiple organ dysfunction syndrome (MODS). Also included are pathologic sequellae associated with insulin-dependent diabetes mellitus (including diabetic retinopathy), lupus nephropathy, Heyman nephritis, membranous nephritis and other forms of glomerulonephritis, contact sensitivity responses, and inflammation resulting from contact of blood with artificial surfaces that can cause complement activation, as occurs, for example, during extracorporeal circulation of blood (e.g., during hemodialysis or via a heart-lung machine, for example, in association with vascular surgery such as coronary artery bypass grafting or heart valve replacement), or in association with contact with other artificial vessel or container surfaces (e.g., ventricular assist devices, artificial heart machines, transfusion tubing, blood storage bags, plasmapheresis, plateletpheresis, and the like). Also included are diseases related to ischemia/reperfusion injury, such as those resulting from transplants, including solid organ transplant, and syndromes such as ischemic reperfusion injury, ischemic colitis and cardiac ischemia. The solid solution capsules comprising Compound 1 described herein may also be useful in the treatment of age-related macular degeneration (Hageman et al, *P.N.A.S.* 102: 7227-7232, 2005).

Cardiovascular and Cerebrovascular Disorders—e.g., myocardial infarction, coronary thrombosis, vascular occlusion, post-surgical vascular reocclusion, atherosclerosis, traumatic central nervous system injury, and ischemic heart disease. In one embodiment, an effective amount of a solid solution capsule comprising Compound 1 described herein may be administered to a patient at risk for myocardial infarction or thrombosis (i.e., a patient who has one or more recognized risk factor for myocardial infarction or thrombosis, such as, but not limited to, obesity, smoking, high blood pressure, hypercholesterolemia, previous or genetic history of myocardial infarction or thrombosis) in order reduce the risk of myocardial infarction or thrombosis.

Diseases of Vasculitis—Vasculitic diseases are characterized by inflammation of the vessels. Infiltration of leukocytes leads to destruction of the vessel walls, and the complement pathway is believed to play a major role in initiating leukocyte migration as well as the resultant damage manifested at the site of inflammation (Vasculitis, Second Edition, Edited by Ball and Bridges, Oxford University Press, pp 47-53, 2008). The solid solution capsules comprising Compound 1 described herein can be used to treat vasculitis, including anti-neutrophil cytoplasmic antibody associate vasculitis (or ANCA-associated vasculitis, which includes microscopic polyangiitis, eosinophilic granulomatosis with polyangitis, and granulomatosis with polyangiitis, which is also known as Wegener's disease), Churg-Strauss syndrome, Henoch-Schonlein purpura, polyateritis nodosa, Rapidly Progressive Glomerulonephritis (RPGN), cryoglobulinaemia, giant cell arteritis (GCA), Behcet's disease and Takayasu's arteritis (TAK).

HIV infection and AIDS—the solid solution capsules comprising Compound 1 described herein may be used to inhibit HIV infection, delay AIDS progression or decrease the severity of symptoms or HIV infection and AIDS.

Neurodegenerative disorders and related diseases—Within further embodiments, the solid solution capsules comprising Compound 1 described herein may be used to treat Alzheimer's disease, multiple sclerosis, and cognitive function decline associated with cardiopulmonary bypass surgery and related procedures.

Cancers—The solid solution capsules comprising Compound 1 described herein are also useful for the treatment of cancers and precancerous conditions in a subject. Specific cancers that can be treated include, but are not limited to, sarcomas, carcinomas, and mixed tumors. Exemplary conditions that may be treated according to the present invention include fibrosarcomas, liposarcomas, chondrosarcomas, osteogenic sarcomas, angiosarcomas, lymphangiosarcomas, synoviomas, mesotheliomas, meningiomas, leukemias, lymphomas, leiomyosarcomas, rhabdomyosarcomas, squamous cell carcinomas, basal cell carcinomas, adenocarcinomas, papillary carcinomas, cystadenocarcinomas, bronchogenic carcinomas, melanomas, renal cell carcinomas, hepatocellular carcinomas, transitional cell carcinomas, choriocarcinomas, seminomas, embryonal carcinomas, wilm's tumors, pleomorphic adenomas, liver cell papillomas, renal tubular adenomas, cystadenomas, papillomas, adenomas, leiomyomas, rhabdomyomas, hemangiomas, lymphangiomas, osteomas, chondromas, lipomas and fibromas.

In some embodiments, the solid solution capsules comprising Compound 1 described herein can be used for the treatment of diseases selected from the group consisting of sepsis (and associated disorders), COPD, rheumatoid arthritis, lupus nephritis and multiple sclerosis.

In some embodiments, the solid solution capsules comprising Compound 1 described herein can be used for the treatment of diseases selected from the group consisting of anti-neutrophil cytoplasmic antibody associate (ANCA) vasculitis, C3 glomerulopathy, hidradenitis suppurativa, and lupus nephritis.

Treatment methods provided herein include, in general, administration to a patient an effective amount of one or more solid solution capsules comprising Compound 1 described herein. Suitable patients include those patients suffering from or susceptible to (i.e., prophylactic treatment) a disorder or disease identified herein. Typical patients for treatment as described herein include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a patient an effective amount of one or more solid solution capsules comprising Compound 1 described herein. In a preferred embodiment, the solid solution capsules comprising Compound 1 described herein are administered to a patient (e.g., a human) orally. The effective amount may be an amount sufficient to modulate C5a receptor activity and/or an amount sufficient to reduce or alleviate the symptoms presented by the patient. Preferably, the amount administered is sufficient to yield a plasma concentration of the compound (or its active metabolite, if the compound is a pro-drug) high enough to detectably inhibit white blood cell (e.g., neutrophil) chemotaxis in vitro. Treatment regimens may vary depending on the compound used and the particular condition to be treated; for treatment of most disorders, a frequency of administration of 4 times daily or less is preferred. In some embodiments, a dosage regimen of 2 times daily is used. In some embodiments, once daily administration is used. The patient may be administered solid solution capsules comprising Compound 1 in a fed or fasted state. In some embodiments, the patient takes the solid solution capsules comprising Compound 1 with food. In some embodiments, the patient takes the solid solution capsules comprising Compound 1 without food. It will be understood, however, that the specific dose level and treatment regimen for any particular patient will depend upon a variety of factors including the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

Dosage levels of the order of from about 0.1 mg to about 140 mg per kilogram of body weight per day are useful in the treatment or preventions of conditions involving pathogenic C5a activity (about 0.5 mg to about 7 g per human patient per day). Dosage unit forms will generally contain between from about 1 mg to about 500 mg of Compound 1. In some embodiments, the dosage unit form comprises 10 mg of Compound 1. It is preferred that sufficient amount of Compound 1 be administered to achieve a serum concentration of 5 ng (nanograms)/mL-10 μg (micrograms)/mL serum, more preferably sufficient Compound 1 to achieve a serum concentration of 20 ng-1 μg/ml serum should be administered, most preferably sufficient Compound 1 to achieve a serum concentration of 50 ng/ml-200 ng/ml serum should be administered.

D. Pharmaceutical Dosage Forms

The present disclosure includes pharmaceutical dosage forms of Compound 1 as a free base, in its neutral form. The dosage forms described herein are solid solution capsules for oral administration to a subject.

As described above, the solid solution capsules can comprise about 1 to 2.8% of compound 1 by weight of the total fill wait of said solution capsule. In some embodiments, the total fill weight of said solid solution capsule is about 130 mg to about 900 mg. Thus, in some embodiments, single unit dosage capsules can include 1.3 mg to 25.2 mg of Compound 1 as a free base, in its neutral form.

In some aspects, the present disclosure provides a single unit dosage capsule comprising about 2.6 mg to 25.2 mg of Compound 1 as a free base, in its neutral form

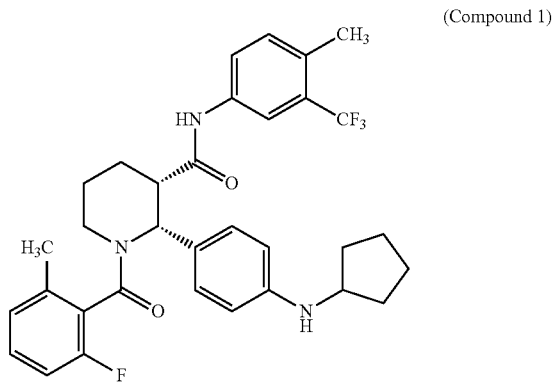 [SMILES: Cc1ccc(NC(=O)[C@H]2CCCN(C(=O)c3c(C)cccc3F)[C@H]2c2ccc(NC3CCCC3)cc2)cc1C(F)(F)F]

(Compound 1)

and a vehicle comprising
  at least one non-ionic surfactant having a hydrophilic-lipophilic balance (HLB) value of at least 10, and
  at least one water-soluble solubilizer having a melting point at or above 37° C.

In some embodiments, the solid solution capsules comprise about 2% of compound 1 by weight of the total fill wait of said solution capsule. In some embodiments, the total fill weight of said solid solution capsule is about 130 mg to about 900 mg. In such embodiments, single unit dosage capsules can include 2.6 mg to 18 mg of Compound 1 as a free base, in its neutral form. In some embodiments, single unit dosage capsules can include 10 mg of Compound 1 as a free base, in its neutral form.

The total fill weight of the single unit dosage capsule is about 100 mg to about 1,000 mg. In some embodiments, the total fill weight of the single unit dosage capsule is about 130 mg to about 900 mg. In some embodiments, the total fill weight of the single unit dosage capsule is about 250 mg to about 750 mg. In some embodiments, the total fill weight of the single unit dosage capsule is about 500 mg.

In some embodiments, the single unit dosage capsule is size #00, #1, #2, #3, #4, or #5. In some embodiments, the single unit dosage capsule is size #0. In some embodiments, the single unit dosage capsule is size #00. In some embodiments, the single unit dosage capsule is size #1. In some embodiments, the single unit capsule is size #2. In some embodiments, the single unit dosage capsule is size #3. In some embodiments, the single unit dosage capsule is size #4. In some embodiments, the single unit dosage capsule is size #5.

In some embodiments, the capsule dosage form is a hard capsule. In some embodiments, the capsule dosage form is a soft capsule.

In some embodiments, the total weight of the vehicle comprises a 30:70 to 65:35 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is between 30:70 and 65:35. In some embodiments, wherein the total weight of the vehicle comprises a 35:65 to 65:35 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is from 35:65 to 65:35. In some embodiments, the total weight of the vehicle comprises a 45:55 to 55:45 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is from 45:55 to 55:45. In some embodiments, the total weight of the vehicle comprises about a 50:50 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is 50:50. In some embodiments, the total weight of the vehicle comprises about a 40:60 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is 40:60. In some embodiments, the total weight of the vehicle comprises about a 30:70 ratio of at least one non-ionic surfactant having an HLB value of at least 10 and at least one water-soluble solubilizer having a melting point at or above 37° C. In a preferred embodiment, the ratio of macrogol-40-glycerol hydroxystearate to polyethylene glycol 4000 (PEG-4000) is 30:70.

E. Kits

The disclosure also encompasses kits comprising a solid solution capsule comprising Compound 1 as described herein.

In some aspects, provided herein are kits comprising a solid solution capsule comprising Compound 1 as described herein. In some embodiments, provided herein are one or more unit dosage capsules described herein.

Some of the kits described herein include a label describing a method of administering a solid solution capsule comprising Compound 1. Some of the kits described herein include a label describing a method of treating a disease or disorder involving pathologic activation of C5a receptors. In some embodiments, the kits described herein include a label describing a method of treating ANCA-associated vasculitis.

The solid solution capsule comprising Compound 1 of the present disclosure can be packaged in a bottle, jar, vial, ampoule, tube, blister pack, or other container-closure system approved by the Food and Drug Administration (FDA) or other regulatory body, which may provide one or more unit dosages containing solid solution capsules comprising Compound 1 or a phamectucially acceptable salt thereof. In some embodiments, the solid solution capsule comprising Compound 1 is packaged in a bottle. The package or dispenser may also be accompanied by a notice associated with the container in a form prescribed by a governmental agency regulating the manufacture, use, or sale of pharmaceuticals, the notice indicating approval by the agency. In certain aspects, the kit may include a solid solution capsule comprising Compound 1 as described herein, a container closure system including the formulation or one or more dosage units form including the formulation, and a notice or instructions describing a method of use as described herein.

IV. Examples

Example 1: Free Base Compound 1 Exhibits Poor Solubility

The solubility of Compound 1 in pH adjusted buffer solutions (from pH 2 to 12), in water, in 0.1M HCl, and in Simulated Gastric Fluid (SGF), in Fed- and Fasted-State Simulated Intestinal Fluid (FeSSIF, FaSSIF) were evaluated, the data are shown in Table 1, below, and FIG. 1.

TABLE 1

| pH Solubility Profile of Compound 1 | | |
|---|---|---|
| Solvent | Actual pH | μg/mL |
| pH 2 Buffer | 1.99 | 0.863 |
| pH 3 Buffer | 3.01 | 0.101 |
| pH 4 Buffer | 4.01 | 0.013 |
| pH 5 Buffer | 5.00 | 0.021 |
| pH 6 Buffer | 6.00 | 0.021 |
| pH 7 Buffer | 7.03 | 0.053 |
| pH 8 Buffer | 8.00 | 0.068 |
| pH 9 Buffer | 9.00 | 0.101 |
| pH 10 Buffer | 9.95 | 0.030 |
| Water | 5.92 | 0.008 |
| 0.1N HCl | 1.05 | 8.050 |
| SGF, pH 1.6 | 1.39 | 2.645 |
| FeSSIF, pH 5 | 4.98 | 2.092 |
| FeSSIF, pH 6.5 | 6.47 | 1.961 |
| FaSSIF, pH 6.5 | 6.47 | 0.656 |

Compound 1 free base has very poor aqueous solubility across full spectrum of pH range, including the biorelevant media and water (no salt effect).

Example 2: Preparing a Liquid Formulations of PEG400/EtOH and Compound 1

Liquid formulations of PEG400/EtOH and Compound 1 can be prepared using general methods for making liquid formulations known in the art. For example, Compound 1 was dissolved in EtOH with agitation and ambient temperature, then the desired amount of PEG400 was added to achieve the desired ratios.

All three concentration formulations in PEG-400/Ethanol stored at Refrigerated Stability (5° C./Ambient), Room Temperature (25° C./60% RH), Normal Laboratory Light Conditions, and Accelerated Stability (40° C./75% RH) appeared stable after 1 week, the Compound 1 assay values ranged from 98.1-103.1% of label claim. The total impurities found in all formulations after 1 week were in the range of 0.28-0.34% a/a of the total peaks; the highest individual impurity was reported at 0.17% a/a with a relative retention time of 0.90-0.94

Despite these results, formulations with ethanol can introduce dosing inaccuracy and undissolved drugs due to evaporation of the ethanol during both dose preparation and storage. As such, formulations with ethanol do not provide the needed attributes.

Example 3: Exploring Alternative Excipients for Liquid Formulations with Compound 1

The liquid formulations of the present example are prepared as described in Example 2. When additional excipients are included, they are added after dissolution of Compound 1 in ethanol.

The data from this test is summarized in Table 2, below.

TABLE 2

Alternative Excipients/Solvents Tested

| Formulations | Solubility (mg/mL) | Additional Observations |
| --- | --- | --- |
| PEG400/Propylene Glycol (50/50 v/v) | 10.87 | Somewhat dissolved overnight, however, precipitation with the addition of cranberry juice. |
| PEG400/EtOH/Solutol HS 15 (50/45/5 v/v) | ~30 (Visually) | Visual assessment of solubility based on a control solution of PEG400/EtOH (50/50% v/v) with 30 mg/mL, Compound 1 is not fully soluble in control vehicle. A few API particles left overnight, did not attempt cranberry juice. |
| PEG400/EtOH/Solutol HS 15 (50/40/10 v/v) | ~30 (Visually) | Visual assessment of solubility based on a control solution of PEG400/EtOH (50/50% v/v) with 30 mg/mL, Compound 1 is not fully soluble in control vehicle. A few API particles left overnight, did not attempt cranberry juice. |
| PEG400/EtOH/Transcutol P (50/45/5 v/v) | ~30 (Visually) | Visual assessment of solubility based on a control solution of PEG400/EtOH (50/50% v/v) with 30 mg/mL, Compound 1 is not fully soluble in control vehicle. A few API particles left overnight, did not attempt cranberry juice. |
| PEG400/EtOH/Transcutol P (50/40/10 v/v) | ~30 (Visually) | Visual assessment of solubility based on a control solution of PEG400/EtOH (50/50% v/v) with 30 mg/mL, Compound 1 is not fully soluble in control vehicle. A few API particles left overnight, did not attempt cranberry juice. |
| PEG400/EtOH/Solutol HS 15 (70/25/5 v/v) | 20.0 | Precipitate forms in cranberry juice. |
| PEG400/EtOH/Solutol HS 15 (70/20/10 v/v) | 20.4 | Slow to precipitate with addition to cranberry juice. Mixture was a smooth suspension. No further work done using Solutol, unknown oral toxicity from feedback from supplier to ChemoCentryx. |
| PEG400/EtOH/Transcutol P (50/45/5 v/v) | 19.9 | Fine precipitate forms in cranberry juice to give a dispersed mixture of small particles, particles not readily noticeable compared to in Solutol, resulting in a smooth solution lasting a couple of hours. |
| PEG400/EtOH/Transcutol P (50/40/10 v/v) | 20.2 | Fine precipitate forms in cranberry juice to give a dispersed mixture of small particles, particles not readily noticeable compared to in Solutol, resulting in a smooth solution lasting a couple of hours. |
| Captisol in water (40% w/v) | 0.01 | API undissolved overnight even with warming to 60°. |
| Cavitron W7 HP5 in water (40% w/v) | 0.05 | API undissolved overnight even with warming to 60°. |
| PEG400/EtOH/Cremophor EL (50/45/5 v/v) | Prepared 20 mg/mL formulation | A translucent solution with floating fine particles. |
| PEG400/EtOH/Cremophor EL (50/40/10 v/v) | Prepared 20 mg/mL formulation | Initial solution containing Cremophor EL was translucent; solution became clear upon adding of cranberry juice. Observation under microscope shows no undissolved API particles, appearance similar to placebo vehicles. |
| PEG400/EtOH/Cremophor EL (70/25/5 v/v) | Prepared 20 mg/mL formulation | A translucent solution. |
| PEG400/EtOH/Cremophor EL (70/20/10 v/v) | Prepared 20 mg/mL formulation | Initial solution containing Cremophor EL was translucent; solution became clear upon adding of cranberry juice. Observation under microscope shows no undissolved API particles, appearance similar to placebo vehicles. |

TABLE 2-continued

Alternative Excipients/Solvents Tested

| Formulations | Solubility (mg/mL) | Additional Observations |
|---|---|---|
| PEG400/EtOH/Transcutol P (50/40/10 v/v) | Prepared 20 mg/mL formulation | Initial solution containing Cremophor EL was translucent; solution became clear upon adding of cranberry juice. Observation under microscope shows no undissolved API particles, appearance similar to placebo vehicles. |
| PEG400/EtOH/Transcutol P (70/20/10 v/v) | Prepared 20 mg/mL formulation | Initial solution containing Cremophor EL was translucent; solution became clear upon adding of cranberry juice. Observation under microscope shows no undissolved API particles, appearance similar to placebo vehicles. |
| Miglyol 810 | Not tested | Immiscible in the presence of PEG400 at ratios of 30-70%, even on adding the ethanol. |

Particular formulations tested herein provided completely dissolved Compound 1. Despite this promise, the most positive formulations each included ethanol, which as described in Example 2 can introduce dosing inaccuracy and undissolved drugs due to evaporation of the ethanol during both dose preparation and storage.

Example 4: Preparing Solid Solution Capsules Comprising Compound 1 in a 50:50 Mixture of Macrogol-40-Glycerol Hydroxystearate:PEG-4000

Manufacture of Compound 1 solid solution capsules utilized a traditional pharmaceutical oral dosage form equipment suitable for filling hard gelatin capsules. The capsule fill mass is a standard heated stainless steel vessel with agitator/homogenizer.

A list of typical equipment required for the manufacturing process is found in Table 3. Equipment examples are listed for information purpose only.

TABLE 3

Equipment Used in the Manufacture

| Manufacturing Step | Equipment type | Equipment Example |
|---|---|---|
| Melting of Macrogol-Glycerol Hydroxystearate | Heating oven | Despatch drying oven or equivalent |
| Compound 1 desagglomeration | Screening mill | Quadro Comill or equivalent |
| Compounding | Jacketed stainless steel mixing vessel | Olsa mixer homogenizer 150 Liter or equivalent |
| Encapsulation | Encapsulator with volume displacement | Shionogi F40 filler or equivalent |
| Capsule banding | Capsule banding machine | Shionogi S40 capsule bander or equivalent |
| Check weighing | Weight sorter | Qualicaps CWI-90 weight sorter or equivalent |
| Metal detection | Metal Detector | Lock Insight PH Metal Detector or equivalent |
| Primary packaging | Automated commercial packaging line | Deckert capsule counting and pot filling line or equivalent |

The in-process controls for the drug product manufacturing process are summarized in Table 4.

TABLE 4

In-Process Controls for Compound 1 10 mg Hard Capsule

| Step | In-process Test | Analytical Procedure | In-Process Limit |
|---|---|---|---|
| Mixing | DS dissolution | Centrifuge test | Absence of undissolved drug substance |
| Mixing | DS dissolution Verification | Visual | Clear Solution |
| Encapsulation | Individual Weight | Weigh | T1 ± 3%; T2 ± 5% |
|  | Appearance | Visual | No defect on the capsule surface |
| Weight Check/ Inspection | Appearance | Visual | Per Site AQL |
|  | Individual Weight | Weigh | Target ± 5% |
| Packaging | Cap Torque | Torque Tester | Sufficient to engage CR Feature |
|  | Seal Integrity | Visual | Seal Intact |

In addition to the visual test for verification of the drug substance dissolution, a centrifuge test was performed. From the vessel a sample was taken, centrifuged and controlled for absence of undissolved drug substance. If the drug substance is not fully dissolved, white particles are visible at the tip of the centrifuge tube.

Solid solution 10 mg capsules of Compound 1 are prepared with the components summarized in Table 5.

TABLE 5

Composition of Compound 1 10 mg Hard Capsule

|  |  | 10 mg Capsule | |
|---|---|---|---|
| Component | Function | (mg) | % (w/w) |
| Compound 1 | Drug Substance | 10.0 | 2.0 |
| Macrogol-Glycerol Hydroxystearate (e.g. Cremophor RH40) | Vehicle/Solubilizer | 245.0 | 49.0 |
| Polyethylene glycol 4000 (PEG-4000) | Vehicle/Solubilizer | 245.0 | 49.0 |
| Total Fill Per Capsule |  | 500.0 | 100% |
| Hard gelatin capsule, light orange opaque/ yellow opaque, Size 0 | Capsule shell | 96 Approx. | NA |
| Gelatin sealing band | Capsule sealant | 5 Approx. | NA |
| Total |  | 601 Approx. | NA |

Figure 2:
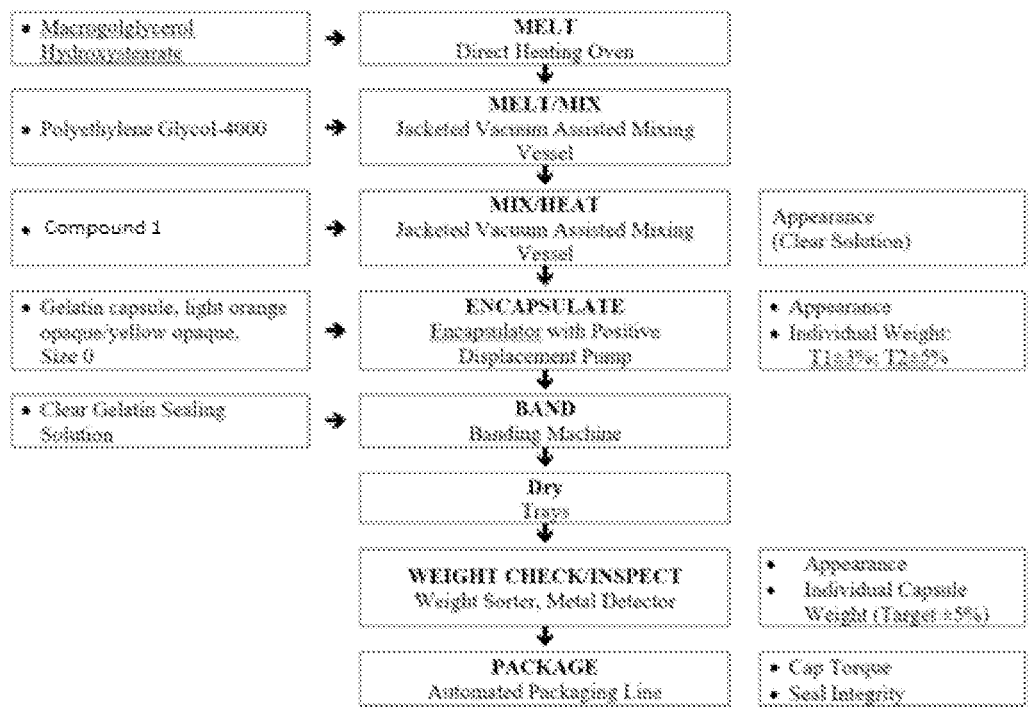
FIG. 2 illustrates the flow diagram for making a solid solution capsule formulation comprising Compound 1.

The solid solution formulations of Table 5 were prepared according the manufacturing process shown in FIG. 2. The steps used are further detailed below:

1. Macrogol-Glycerol Hydroxystearate was melted in a direct heating oven at 60±10° C.
2. Polyethylene glycol-4000 (PEG-4000) was melted in a jacketed mixing tank at approximately 80-85° C. Stirring begins once the PEG-4000 is largely dissolved.
3. The jacketed mixing tank with the melted PEG-4000 was cooled to 60±10° C. The melted Macrogol-Glycerol Hydroxystearate is added to the tank and mixed under vacuum to deaerate the solution.
4. Compound 1 was added to the mixing tank and fully dissolved with stirring at 60±5° C. for at least 3.5 hours.
5. The size 0 capsules were filled to the target 500 mg fill weight using an automated encapsulator fitted with a positive displacement pump. The fill solution in the jacketed encapsulator hopper was maintained at approximately 60-65° C. during the capsule filling operation.
6. The filled capsules were sealed with a gelatin band which is maintained at approximately 50-55° C.
7. The finished capsules were dried on trays at room temperature.

The composition of the Gelatin Capsule Shell and Gelatin sealing solution are described in Table 6 and Table 7, respectively

TABLE 6

Composition of Size 0 Hard Gelatin Capsule Shell

|  |  | Quantity per Capsule | |
|---|---|---|---|
| Component | Function | (mg) | % (w/w) |
| Cap: Light Orange Opaque | | | |
| Red Iron Oxide | Colorant | 0.24 | 0.25 |
| Yellow Iron Oxide | Colorant | 0.24 | 0.25 |
| Titanium Dioxide | Colorant | 1.92 | 2 |
| Gelatin | Structure | 93.60 | 97.5 (q.s.) |
| Body: Yellow Opaque | | | |
| Yellow Iron Oxide | Colorant | 0.24 | 0.25 |
| Titanium Dioxide | Colorant | 1.92 | 2 |
| Gelatin | Structure | 93.84 | 97.75 (q.s.) |
| Capsule Weight (0 size) |  | 96 ± 6 | NA | q.s. = quantity sufficient

TABLE 7

Composition of Gelatin Sealing Solution

|  |  | 10 mg Capsule | |
|---|---|---|---|
| Component | Function | (mg) | % (w/w) |
| Gelatin | Sealant | 4.8 | 21.7 |
| Polysorbate 80 | Plasticizer | 0.2 | 0.9 |
| Water, Purified[a] | Solvent | 17.0 | 77.4 |
| Total Per Capsule |  | ca. 5 mg | 100% |

[a]Removed during processing

Example 5: Testing Alternative Macrogol-40-Glycerol Hydroxystearate:PEG-4000 Formulations Using the general procedures outlined in Example 4, formulations of macrogol-40-glycerol hydroxystearate: PEG-4000 were prepared (50:50, 70:30, 30:70, and 90:10 (w/w) macrogol-40-glycerol hydroxystearate:PEG-4000).

Figure 3:
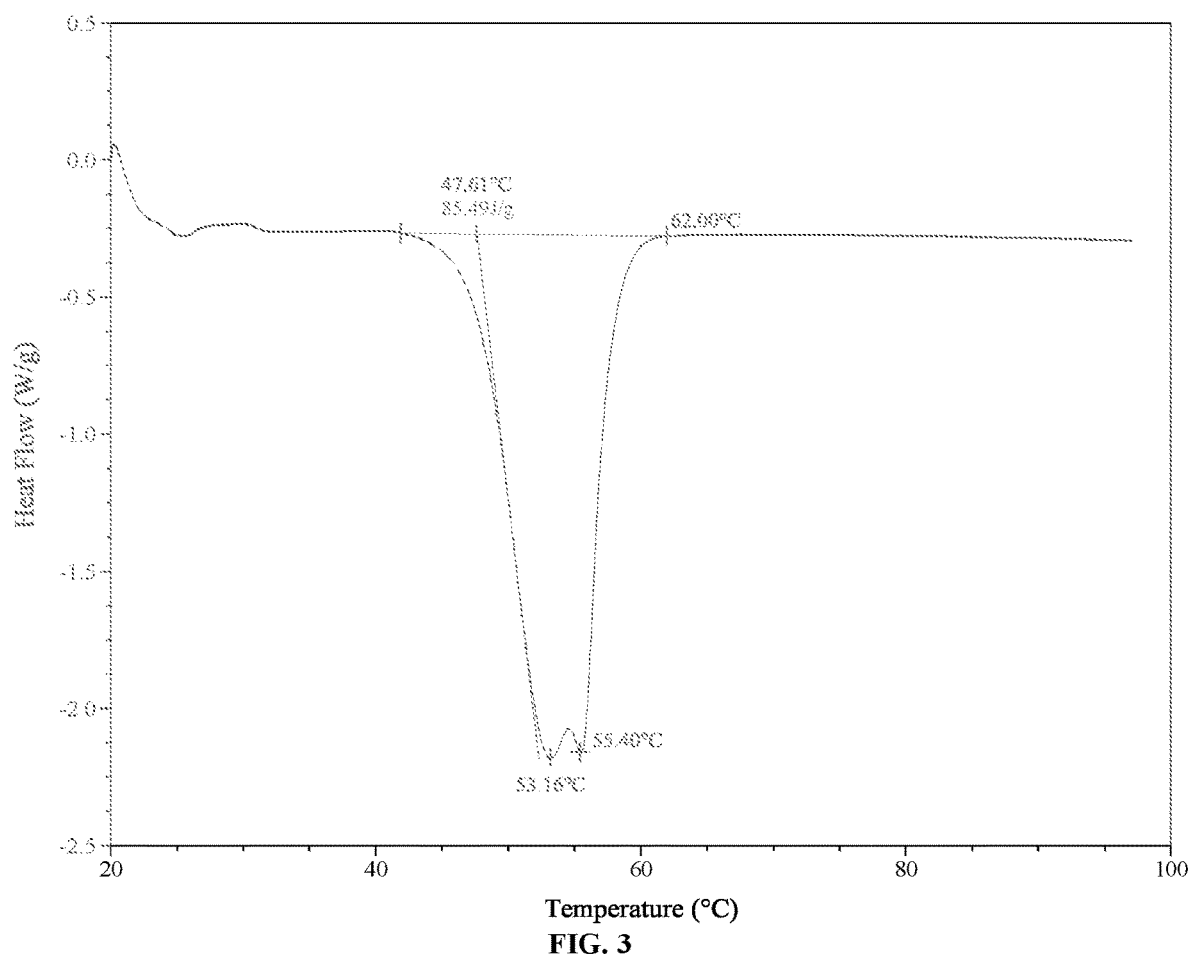
FIG. 3 is a differential scanning calorimetry (DSC) plot of a solid solution capsule comprising Compound 1 in a 50:50 mixture of Macrogol-40-Glycerol Hydroxystearate:PEG-4000
Figure 4:
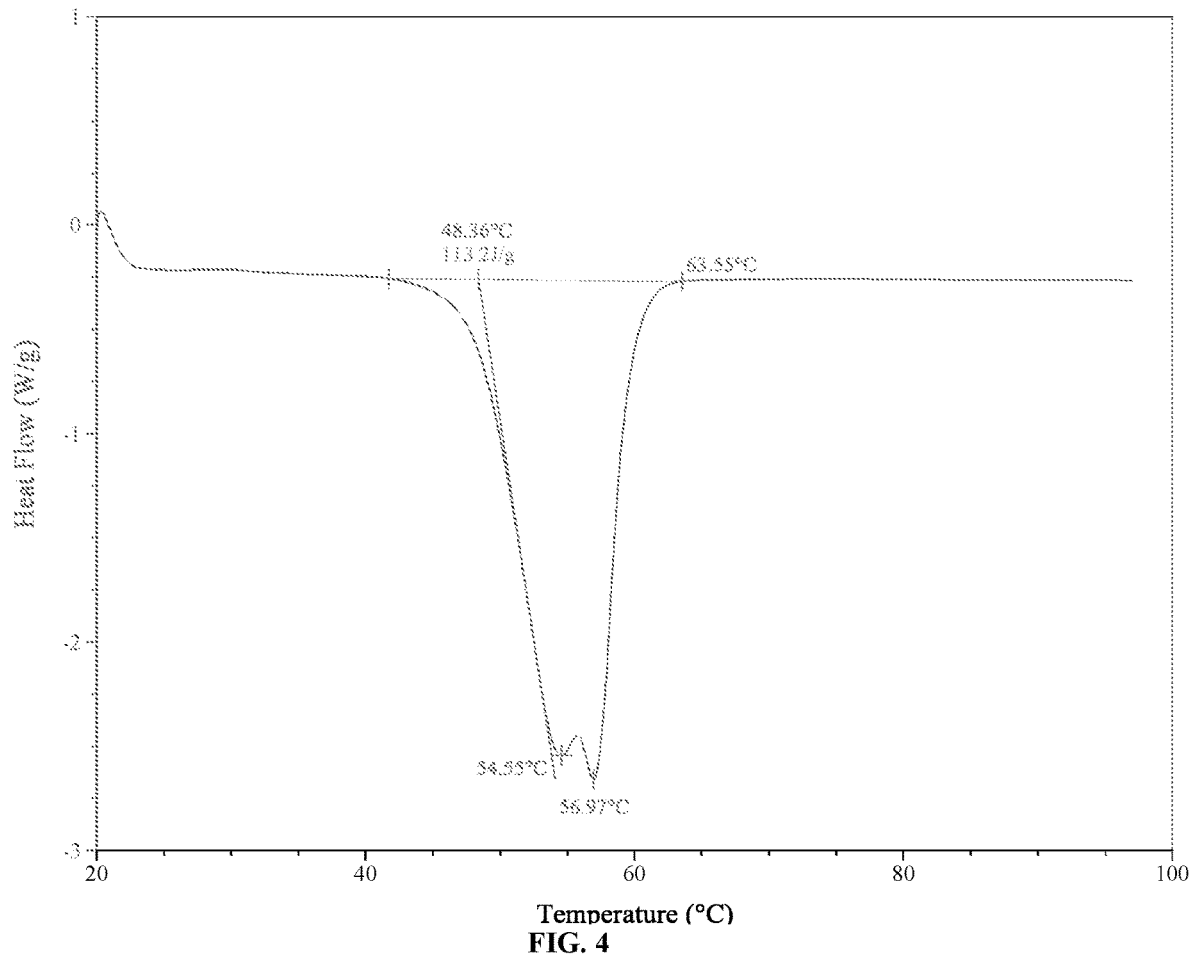
FIG. 4 is a DSC plot of a solid solution capsule comprising Compound 1 in a 30:70 mixture of Macrogol-40-Glycerol Hydroxystearate:PEG-4000

Each of the prepared formulations were characterized using differential scanning calorimetry (DSC). Formulations comprising macrogol-40-glycerol hydroxystearate:PEG-4000 at 50:50 & 30:70 appear to have one broad endothermic peak in the DSC thermograms, implying one miscible solid phase (see, FIG. 3 and FIG. 4, respectively). Comparatively, formulations comprising macrogol-40-glycerol hydroxystearate:PEG-4000 formulations having 90:10 &

Figure 5:
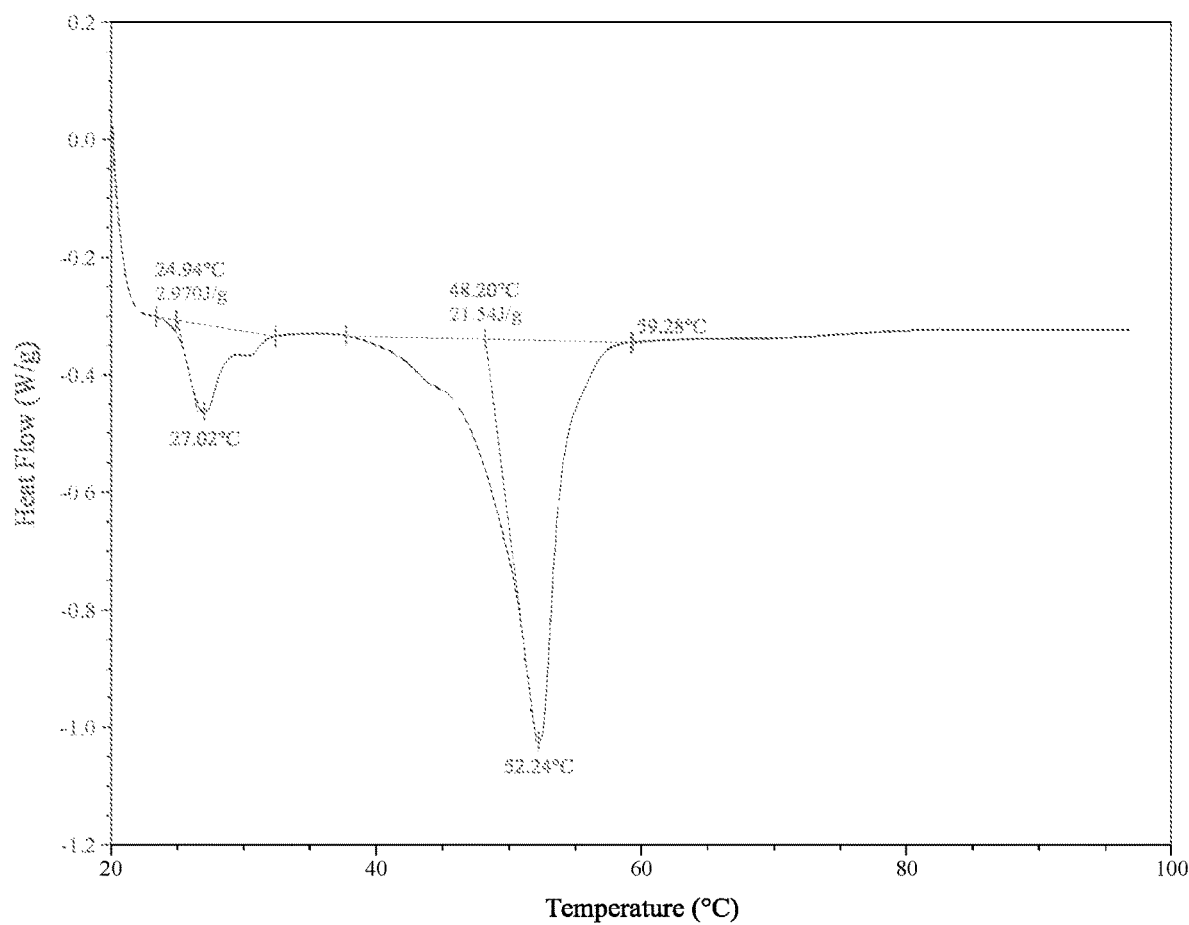
FIG. 5 is a DSC plot of a solid solution capsule comprising Compound 1 in a 90:10 mixture of Macrogol-40-Glycerol Hydroxystearate:PEG-4000.

70:30 show two separate endothermic peaks in the DSC thermograms, indicating potential phase separation (see, FIG. 5 and data not show).

Example 6: Dissolution Profile of Solid Solution Capsule Comprising Compound 1

Solid Solution capsules of Compound 1 comprising 30:70, and 50:50 (w/w) macrogol-40-glycerol hydroxystearate:PEG-4000 were prepared as described in Example 4.

The USP Apparatus II (paddles) with 900 mL media volume at 37.0±0.5° C. was selected for the dissolution development studies. Vessels are 1000 mL, clear glass, round-bottom. Media represents physiologic conditions. Paddles with sinkers were selected over baskets to ensure sufficient agitation during the dissolution test and to maintain the capsule in the paddle agitation zone during disintegration.

Figure 6:
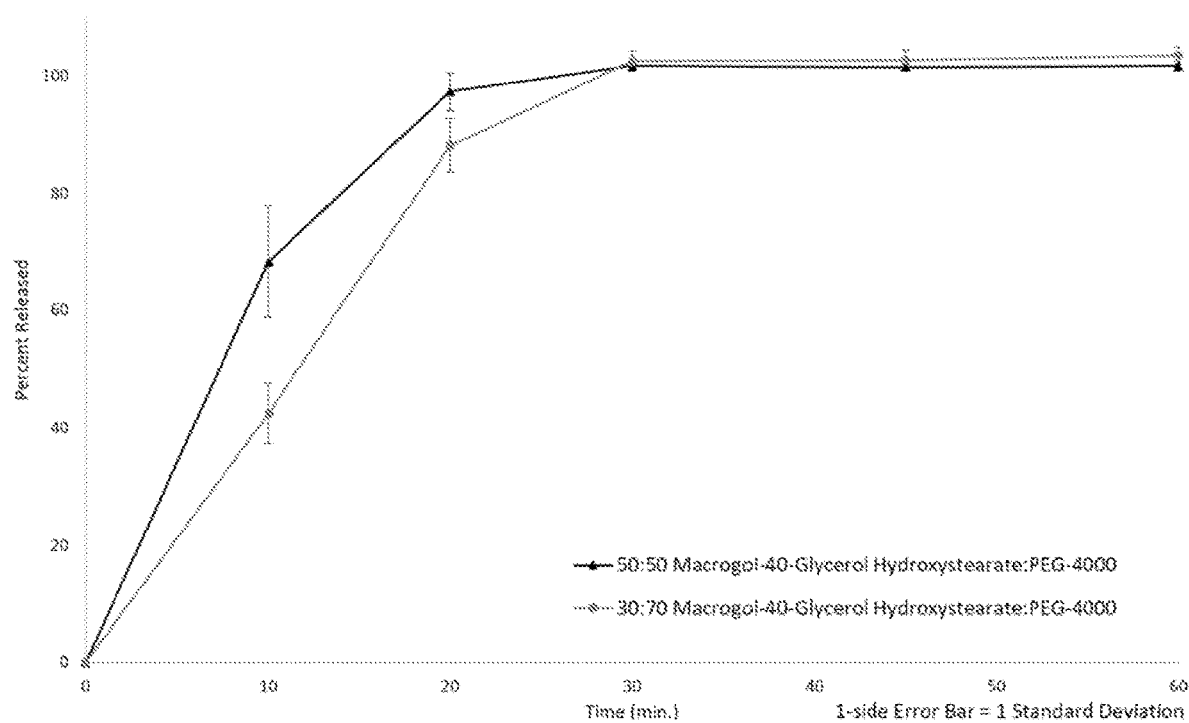
FIG. 6 plots the dissolution profile of various Macrogol-40-Glycerol Hydroxystearate:PEG-4000 blends.

FIG. 6 plots the dissolution of each sample tested. The 50:50 macrogol-40-glycerol hydroxystearate:PEG-4000 sample demonstrated rapid dissolution, while the 30:70 macrogol-40-glycerol hydroxystearate:PEG-4000 sample demonstrated slower initial dissolution characteristics.

Figure 7:
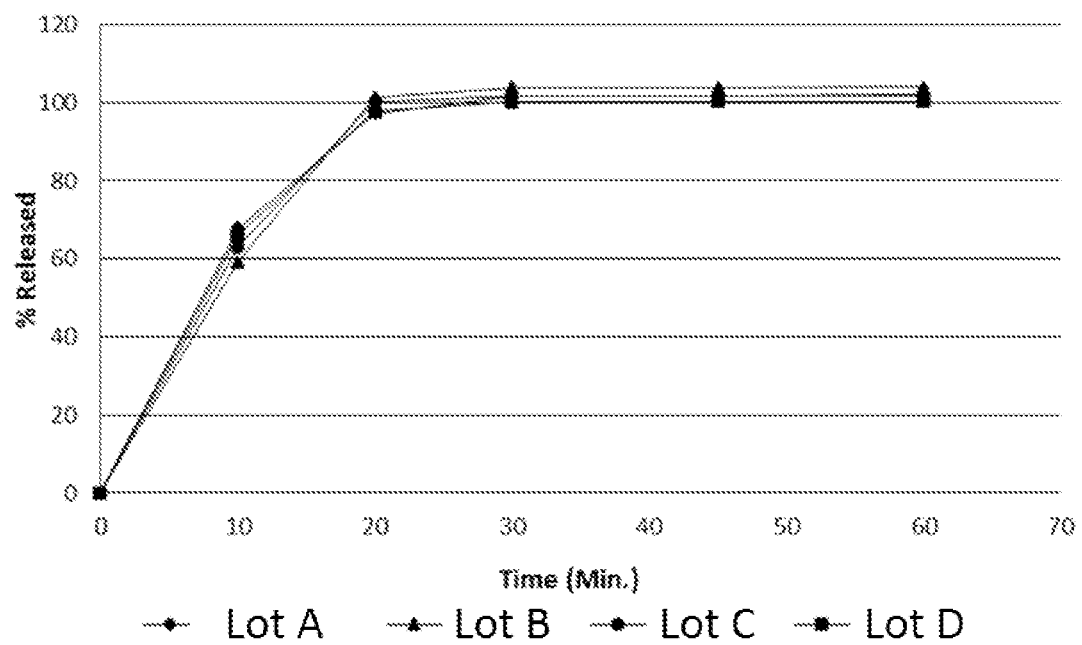
FIG. 7 plots the dissolution profile of Lots A, B, C, and D of a solid solution capsule comprising Compound 1 in a 50:50 mixture of Macrogol-40-Glycerol Hydroxystearate:PEG-4000.

To confirm reproducibility of the 50:50 macrogol-40-glycerol hydroxystearate:PEG-4000 blend, samples from multiple lots preparing the 50:50 formulation were tested. Indeed, FIG. 7 demonstrates that fast, reproducible release of Compound 1 is achieved.

Example 7: Forced Degradation of Solid Solution Capsule Comprising Compound 1 in a 50:50 Mixture of Macrogol-40-Glycerol Hydroxystearate:PEG-4000

The identification of forced degradation products in Compound 1 solid solution capsules was performed using HPLC with photodiode array detection. Capsules were exposed to stress conditions (acid, base, peroxide, heat, light, heat and humidity) and chromatograms and data from the stressed samples were then compared to an unstressed control sample. Only those degradation products found in the stressed samples but not in the unstressed control sample were reported. A summary of the results under the stressed conditions are summarized in Table 9 for the capsule and in Table 10 for the degradation products found for the stressed capsules. Details of each condition tested are shown in Table 8. Under all of the stress conditions studied, the Compound 1 peak showed no co-elution or interference from potential degradation products based upon the peak purity results from diode array detection.

TABLE 9

Summary of Assay and Peak Purity for Compound 1 10 mg Hard Capsule Forced Degradation Studies

| Stress Conditions | Sample | % Compound 1 Recovery | Peak Purity Angle | Peak Purity Threshold | Peak is Pure?[1] |
|---|---|---|---|---|---|
| Control | Whole Capsules | 97.8 | 0.113 | 0.663 | Yes |
| Acid Hydrolysis | | 96.4 | 0.099 | 0.571 | Yes |
| Base Hydrolysis | | 105.4 | 0.294 | 2.311 | Yes |
| Oxidation | | 73.3 | 0.101 | 0.349 | Yes |
| Heat (80° C.) | | 100.9 | 0.117 | 0.723 | Yes |
| Heat and Humidity (40° C./75% RH) | | 97.5 | 0.131 | 0.660 | Yes |

[1]Peak is spectrally homogeneous if the Peak Purity Angle < Peak Purity Threshold

TABLE 10

Summary of Degradation Products Found under Forced Degradation Conditions for Hard Capsules

| Stressed Condition | Relative Retention Time (RRT) | % Found | % Total Related Substances | % Mass Balance |
|---|---|---|---|---|
| Control | 0.780* | 0.06 | 0.06 | 97.8 |
| Acid Hydrolysis | 0.394 | 0.06 | 0.22 | 96.6 |
| | 0.716 | 0.09 | | |
| | 0.780* | 0.07 | | |
| Base Hydrolysis | 0.837 | 0.07 | 0.17 | 105.6 |
| | 0.856 | 0.09 | | |
| Oxidation | 0.707 | 0.51 | 25.50 | 98.8 |
| | 0.781* | 0.11 | | |
| | 0.798 | 4.70 | | |
| | 0.806 | 3.29 | | |
| | 0.867 | 0.29 | | |
| | 0.892 | 0.18 | | |
| | 0.931 | 8.10 | | |
| | 1.112 | 0.07 | | |
| | 1.179 | 0.43 | | |
| | 1.208 | 5.47 | | |
| | 1.233 | 0.15 | | |
| | 1.313 | 1.97 | | |
| | 1.443 | 0.09 | | |
| | 1.488 | 0.06 | | |
| | 1.547 | 0.08 | | |
| Heat (80° C.) | 0.780* | 0.12 | 0.12 | 101.0 |
| Heat and Humidity (40° C./75% RH) | 0.779* | 0.07 | 0.07 | 97.6 |

*Aniline (C0332414), RRT ~0.78

No degradation was observed for placebo capsules at the stress conditions evaluated.

Compound 1 capsules were found to degrade the most under oxidative stress, where a total of fifteen (15) degradants were observed. Acid hydrolysis resulted in three (3)

TABLE 8

Forced Degradation Exposure Conditions (5 capsules per condition)

| Stress Condition | Volume of Reagent Solution (mL) | Temperature (° C.) | Duration | Volume Neutralizing Agent (mL) |
|---|---|---|---|---|
| Acid | 10 mL 10N HCl | Ambient | 24 hours | 10 mL 10N NaOH |
| Base | 10 mL 10N NaOH | Ambient | 24 hours | 10 mL 10N HCl |
| Oxidation | 10 mL 30% $H_2O_2$ | Ambient | 24 hours | 10 mL 30% $Na_2SO_3$ |
| Heat[a] | NA | 80° C. | 3 days | NA |
| Heat and Humidity[a] | NA | 40° C./75% RH | 3 days | NA |
| Photostability[a] | NA | Ambient | Per ICH Q1B | NA |

[a]Samples prepared per capsule assay method;
NA—Not Applicable degradants, base hydrolysis produced two (2) degradants, and heat and heat/humidity produced a single degradant (RRT 0.78). The impurity at an RRT of 0.78 increased only slightly under heat (80° C.) and oxidative stress but did not change under acidic, or basic conditions.

Overall, this study shows that the Compound 1 solid solution capsules are quite stable when exposed to all stress conditions, with the exception of oxidative stress.

Example 8: Pharmacokinetic Data of Solid Solution Capsule in Dogs

Figure 8:
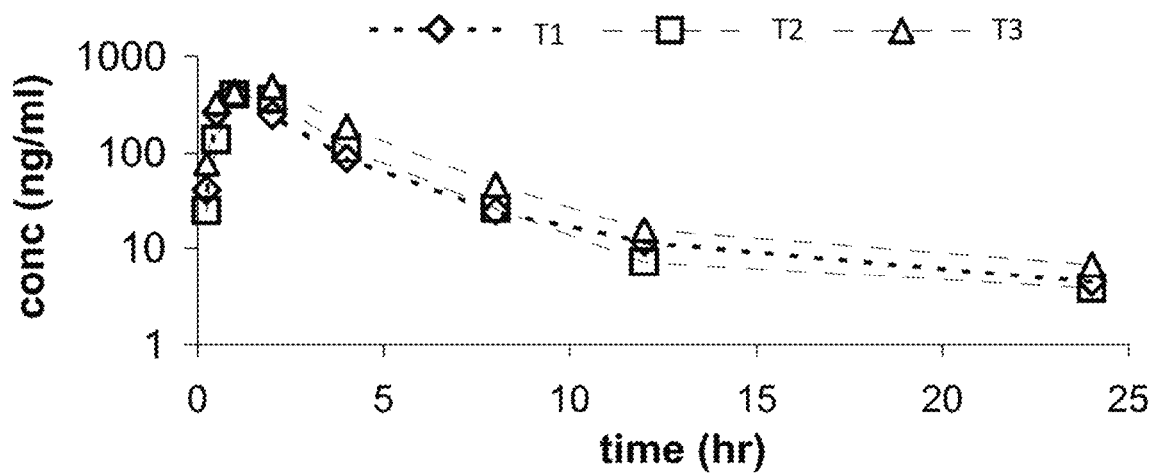
FIG. 8 shows the PK profile of a solid solution capsule comprising Compound 1 in a 50:50 mixture of Macrogol-40-Glycerol Hydroxystearate:PEG-4000 administered to a beagle dog. 20 mg/dog was administered; T1 is trial 1; T2, is trial 2; and T3 is trial 3.
Figure 9:
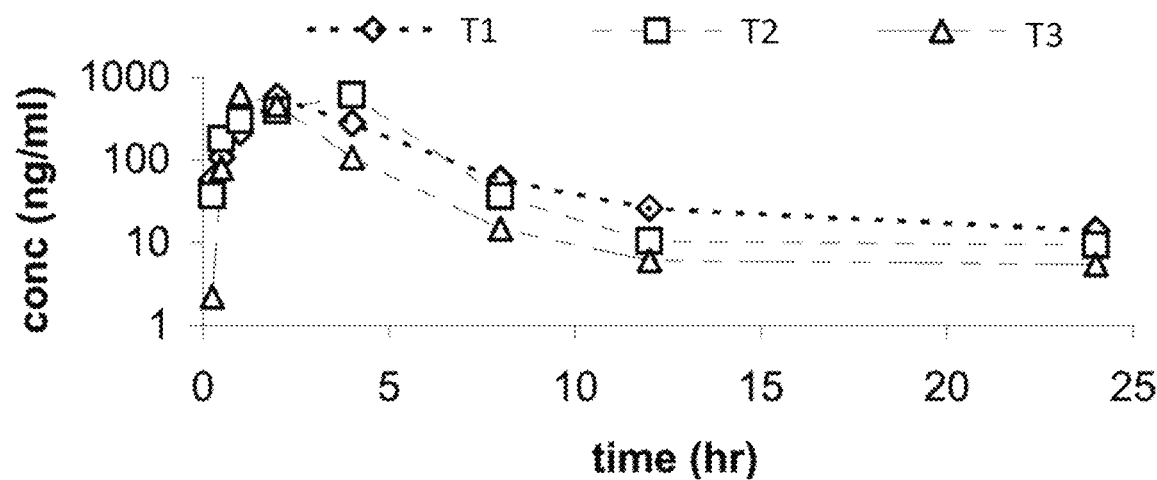
FIG. 9 shows the PK profile of a solid solution capsule comprising Compound 1 in 100% Macrogol-40-Glycerol Hydroxystearate administered to a beagle dog. 20 mg/dog was administered; T1 is trial 1; T2, is trial 2; and T3 is trial 3.

Solid Solution capsules of Compound 1 comprising 50:50 macrogol-40-glycerol hydroxystearate:PEG-4000 or 100% macrogol-40-glycerol hydroxystearate were prepared using the general procedures described in Example 4. The PEG heating steps were omitted for the 100% macrogol-40 glycerol hydroxystearate formulations. These formulations were dosed in beagle dogs (male) at 20 mg per dog to evaluate the pharmacokinetic profile. The results are summarized in Table 11 (below, and shown in FIG. 8 (50:50 macrogol-40-glycerol hydroxystearate:PEG-4000 and FIG. 9 (100% macrogol-40-glycerol hydroxystearate).

Example 9: Pharmacokinetic Data of Solid Solution Capsule in Humans with ANCA Associate Vasculitis Solid Solution capsules of Compound 1 comprising 50:50 macrogol-40-glycerol hydroxystearate:PEG-4000 were prepared using the general procedures described in Example 4.

Patients with AAV were randomized and double-blind in placebo-controlled clinical trial conducted in a step-wise manner to evaluate the efficacy and safety of Compound 1 formulated in a solid solution as described above with reduced or no prednisone in comparison with the standard of care full dose prednisone. All patients received either cyclophosphamide (CYC) or rituximab (RTX) intravenously. 22 subjects received 30 mg of Compound 1 as described above b.i.d. for 84 days and no prednisone (prednisone-matching placebo), 22 subjects received 30 mg Compound 1 as described above b.i.d. for 84 days plus a reduced starting dose (i.e., 20 mg/day) of prednisone, and 23 subjects received Compound 1 as described above—matching placebo b.i.d. for 84 days plus a full starting dose of prednisone (i.e., 60 mg/day). All subjects received IV cyclophosphamide or rituximab.

TABLE 11

Summary of Dog Pharmacokinetic data when administered 20 mg/dog Compound 1

| | PO: 20 mg/dog in 100% macrogol-40-glycerol hydroxystearate Plasma conc. [ng/mL] | | | | | PO: 20 mg/dog in 50:50 mixture of macrogol-40-glycerol hydroxystearate:PEG-4000 Plasma conc. [ng/mL] | | | | |
|---|---|---|---|---|---|---|---|---|---|---|
| Time [hr] | T1 | T2 | T3 | SD | Average | T1 | T2 | T3 | SD | Average |
| $C_{max}$ [ng/mL] | 590 | 604 | 628 | 19.2 | 607 | 411 | 396 | 481 | 45.4 | 429 |
| $AUC_{inf}$ [ng·h/mL] | 2658 | 3015 | 1662 | 701 | 2445 | 1306 | 1443 | 2153 | 455 | 1634 |
| $AUC_{0-t}$ [ng·h/mL] | 2470 | 2996 | 1647 | 680 | 2371 | 1260 | 1394 | 2083 | 442 | 1579 |
| MRT [hr] | 7.1 | 4.2 | 3.2 | 2.0 | 4.8 | 4.8 | 4.5 | 4.8 | 0.2 | 4.7 |
| $t_{1/2}$ [h] | | | | | | | | | | |
| $T_{max}$ [hr] | 2.0 | 4.0 | 1.0 | 1.5 | 2.3 | 1.0 | 1.0 | 2.0 | 0.6 | 1.3 |

Although the 100% macrogol-40-glycerol hydroxystearate formulation provided high bioavailability (as determined by AUC comparison), the 100% macrogol-40-glycerol hydroxystearate formulation is not as stable. In a side-by side comparison of stability, both formulations dosed in dogs were stored for 3 months at 50° C. The 100% macrogol-40-glycerol hydroxystearate formulation showed an increase in an impurity (RRT 0.78), whereas the 50:50 macrogol-40-glycerol hydroxystearate formulation:PEG-4000 formulation remained unchanged. This demonstrates that the 100% macrogol-40-glycerol hydroxystearate formulation is not suitable for pharmaceutical use, while the 50:50 formulation is suitable for pharmaceutical use.

The PK parameters of Compound 1 and its mean trough concentration are shown in Table 12. Following the first dose of 30 mg Compound 1 on Day 1, Compound 1 was absorbed rapidly. The $AUC_{0-6\ hr}$ and $C_{max}$ of Compound 1 were 580±219 ng·hr/mL and 188±69 ng/mL, respectively (these PK exposures were calculated using data from patients dosed both with and without prednisone). The Day 1 $C_{max}$ of Compound 1 in these AAV patients (without prednisone co-administration: $C_{max}$=166±55.2 ng/mL) was similar to that in healthy subjects who were dosed with the same dosage form, suggesting that there is no meaningful difference between AAV patients and healthy subjects in the exposure of Compound 1 after a single oral dose.

TABLE 12

Summary of Mean Pharmacokinetic Parameters for solid solution sapsules comprising Compound 1 in a 50:50 mixture of macrogol-40-glycerol hydroxystearate:PEG-4000 following oral administration of 30 mg of Compound 1 twice daily Compound 1

| | Treatment | | | | | | | | |
|---|---|---|---|---|---|---|---|---|---|
| | Compound 1 + No Prednisone | | | Compound 1 + Low Dose Prednisone | | | Compound 1 with or without Prednisone | | |
| PK Parameters | Mean | SD | N | Mean | SD | N | Mean | SD | N |
| Day 1 $C_{max}$ (ng/mL) | 166 | 55.2 | 21 | 214 | 76.2 | 18 | 188 | 69.1 | 39 |
| Day 1 $T_{max}$ (hr) | 2.85 | 1.19 | 21 | 2.35 | 1.02 | 18 | 2.62 | 1.13 | 39 |
| Day 1 $AUC_{0-6hr}$ (ng · hr/mL) | 526 | 174 | 21 | 643 | 253 | 18 | 580 | 219 | 39 |
| Days 57-85 $C_{min}$ (ng/mL) | 177 | 44.8 | 5 | 219 | 96.8 | 9 | 204 | 82.6 | 14 |

No significant drug-drug interaction was observed in this study between Compound 1 and concomitant medications prednisone, cyclophosphamide, and rituximab.

Example 10: Food Effect on Solid Solution Capsule Comprising Compound 1 in a 50:50 Mixture of Macrogol-40-Glycerol Hydroxystearate:PEG-4000

An open-label study in 16 healthy volunteers to evaluate the pharmacokinetic effect of a high fat (~50% of total caloric content of the meal), high calorie meal on the solid solution capsule of Compound 1 in a 50:50 mixture of macrogol-40-glycerol hydroxystearate:PEG-4000. Subjects received a single oral dose of 30 mg Compound 1, given in the fed or fasted state. Blood samples were collected for measurement of Compound 1 plasma concentrations.

Figure 10:
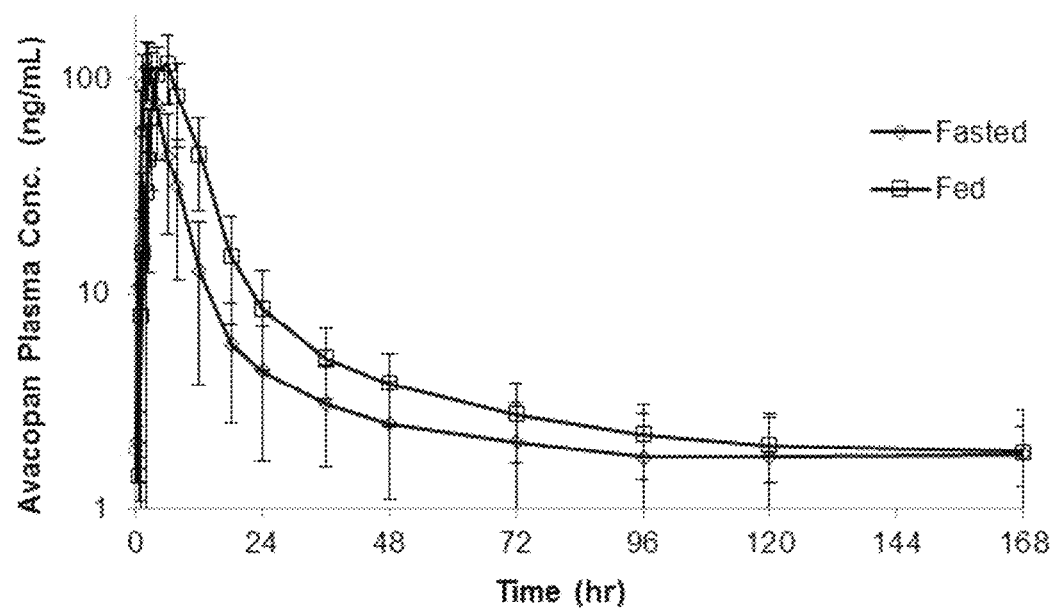
FIG. 10 shows the pharmacokinetic profiles for Compound 1 following a 30 mg single oral dose of Compound 1 with or without a high fat, high calorie meal.

The results of this study showed that administration of a high fat, high calorie meal with 30 mg Compound 1 increased plasma Compound 1 AUC by approximately 70% compared to administration under fasted conditions. $C_{max}$ was more comparable, with only an 8% increase under fed conditions compared to fasted; however, $T_{max}$ was delayed by approximately 3 hours in the fed population (FIG. 10 and Table 13).

Example 11: Stability of the Solid Solution Capsule Formulation

The physical state of the drug substance in solid solution capsules of Compound 1 comprising 50:50 macrogol-40-glycerol hydroxystearate:PEG-4000 prepared as described in Example 4 was assessed in capsules stored for more than 2 years under 65% RH and at 25° C.

Figure 11:
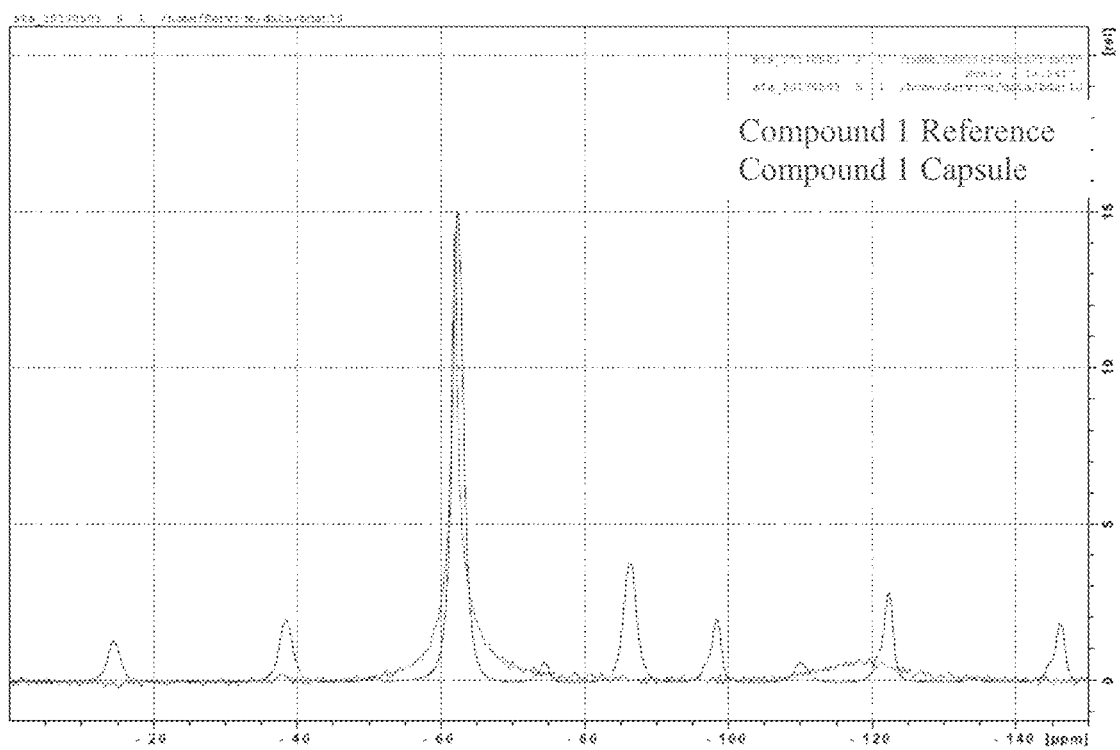
FIG. 11 shows the $^{19}$F Solid-State NMR Spectra of Drug Substance (Ref) and Capsule Fill (9 kHz) from capsules comprising Compound 1 in a 50:50 mixture of Macrogol-40-Glycerol Hydroxystearate:PEG-4000. The Compound 1 Reference sample includes multiple peaks, while the capsule fill (labeled "Compound 1 Capsule") shows significantly fewer peaks.

The capsule fill of select capsules were removed from capsule shells and analyzed using $^{19}F$ solid state nuclear magnetic resonance (SS-NMR). As shown in FIG. 11, no coupling phenomena of the trifluoromethyl (—$CF_3$) and aryl fluoride (CF) groups in the −62 ppm or at −122 ppm regions respectively is observed, which are characteristic of crystalline Compound 1 drug substance. Thus, the drug substance in the capsule fill matrix remained molecularly dissolved in the matrix without any signs of crashing out.

Example 12: Batch Preparation of Solid Solution Capsules comprising Compound 1

Using the general procedures outlined in Example 4, a batch size manufacturing 300,000 units of 10 mg hard

TABLE 13

Comparison of Plasma Compound 1 Pharmacokinetic Parameters Following a 30 mg Single Oral Dose of Compound 1 with or without high fat, high calorie meal

| Parameter | Fed (Test) Geometric LSM | n | Fasted (Reference) Geometric LSM | n | GMR (%) | 90% Confidence Interval | Intra-subject CV % |
|---|---|---|---|---|---|---|---|
| $AUC_{0-t}$ (ng · hr/mL) | 1410.4 | 16 | 826.33 | 16 | 170.68 | 151.09-192.81 | 19.77 |
| $AUC_{0-inf}$ (ng · hr/mL) | 1646.0 | 16 | 959.23 | 14 | 171.60 | 147.12-200.15 | 23.23 |
| $C_{max}$ (ng/mL) | 128.1 | 16 | 118.6 | 16 | 107.98 | 92.05-126.67 | 26.06 |
| $T_{max}$ (hr) | 5.379 | 16 | 2.286 | 16 | 235.29 | 208.37-262.21 | 25.79 |

$AUC_{0-t}$, $AUC_{0-inf}$ and $C_{max}$ parameters were ln-transformed prior to analysis. $T_{max}$ was untransformed.

For ln-transformed PK parameters, geometric least-squares means (LSMs) are calculated by exponentiating the LSMs from ANOVA. For the untransformed parameter $T_{max}$, the LSMs are straight from the ANOVA.

$T_{max}$ is presented as the untransformed LSM.

Geometric least-squares means (LSMs) are calculated by exponentiating the LSMs from the ANOVA.

Geometric Mean Ratio (GMR) = 100 × (test/reference).

For ln-transformed PK parameters, intra-subject CV (% CV) = 100 × (square root (exp[MSE] − 1)).

For the untransformed parameter $T_{max}$, intra-subject CV (% CV) = 100 × (square root [MSE])/(Average of the LSM).

MSE = Residual variance from ANOVA.

capsules was prepared. Amounts used for preparation are shown in Table 14 and Table 15.

TABLE 14

Batch Composition for Compound 1 10 mg Hard Capsule (300,000 Capsules)

| Component | Theoretical Quantity per 300,000 capsule batch |
|---|---|
| Screened Compound 1 | 3.0 kg |
| macrogol-40-glycerol hydroxystearate, USP-NF/Ph.Eur. | 73.5 kg |
| Polyethylene glycol 4000, USP-NF/Ph.Eur. | 73.5 kg |
| Total Capsule Fill | 150 kg |
| Hard gelatin capsule, Size 0, light orange opaque/yellow opaque | 300,000 units (approx. 28.5 kg) |
| Gelatin sealing band[a] | 1.5 kg |
| Total per Batch | 180 kg |

[a]1.5 kg remains per batch after purified water is removed during the process.

TABLE 15

Batch Composition for Gelatin Sealing Banding Solution

| Component | Theoretical Quantity per 13 kg batch |
|---|---|
| Gelatin. USP-NF/Ph.Eur. | 2.8 kg |
| Polysorbate 80, USP-NF/Ph.Eur. | 0.1 kg |
| Purified Water, USP, Ph.Eur | 10.1 kg |
| Total | 13.0 kg |

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A solid solution capsule formulation comprising Compound 1 as a free base, in its neutral form, or in the form of a pharmaceutically acceptable salt

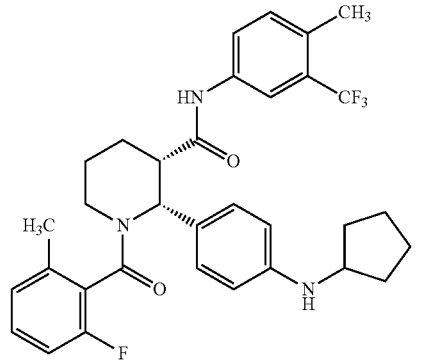

(Compound 1)

and a vehicle comprising
at least one non-ionic surfactant selected from the group consisting of macrogol-40-glycerol hydroxystearate, macrogolglycerol ricinoleate, and macrogol-15-hydroxystearate, and
at least one water-soluble solubilizer selected from the group consisting of PEG-1500, PEG-1540, PEG-2000, PEG-3000, PEG-3350, PEG-4000, PEG-6000, PEG-8000,
wherein
Compound 1 comprises about 1 to 3% by weight of the total fill weight of said solid solution capsule formulation, the vehicle comprises about 97 to 99% by weight of the total fill weight of said solid solution capsule formulation, and
the total weight of the vehicle comprises a 45:55 to 55:45 ratio of the at least one non-ionic surfactant to the at least one water-soluble solubilizer.

2. The solid solution capsule formulation of claim 1 wherein the vehicle comprises about 98% by weight of the total fill weight of said solid solution capsule formulation.

3. The solid solution capsule formulation of claim 1, comprising about 2% of Compound 1 by weight of the total fill weight of said solid solution capsule formulation.

4. The solid solution capsule formulation of claim 1, wherein the total weight of the vehicle comprises about a 50:50 ratio of the at least one non-ionic surfactant to the at least one water-soluble solubilizer.

5. The solid solution capsule formulation of claim 1, wherein the at least one non-ionic surfactant is macrogol-40-glycerol hydroxystearate or macrogolglycerol ricinoleate.

6. The solid solution capsule formulation of claim 1, wherein the at least one non-ionic surfactant is macrogol-40-glycerol hydroxystearate.

7. The solid solution capsule formulation of claim 1, wherein the at least one water-soluble solubilizer is selected from the group consisting of PEG-1540, PEG-2000, PEG-3000, PEG-3350, PEG-4000, PEG-6000.

8. The solid solution capsule formulation of claim 1, wherein the at least one water-soluble solubilizer is PEG-4000.

9. The solid solution capsule formulation of claim 1, wherein the at least one non-ionic surfactant is macrogol-40-glycerol hydroxystearate and the at least one water-soluble solubilizer is PEG-4000.

10. The solid solution capsule formulation of claim 1, wherein the total fill weight of said solid solution capsule is from about 130 mg to 900 mg.

11. The solid solution capsule formulation of claim 1, wherein the total fill weight of said solid solution capsule is about 500 mg.

12. The solid solution capsule formulation of claim 1, wherein the capsule size is #0.

13. The solid solution capsule formulation of claim 1, wherein the capsule is a hard capsule.

14. The solid solution capsule formulation of claim 2, comprising about 2% of Compound 1 by weight of the total fill weight of said solid solution capsule formulation.

15. The solid solution capsule formulation of claim 14, wherein the total weight of the vehicle comprises about a 50:50 ratio of the at least one non-ionic surfactant to the at least one water-soluble solubilizer.

16. The solid solution capsule formulation of claim 15, wherein the at least one non-ionic surfactant is macrogol-40-glycerol hydroxystearate.

17. The solid solution capsule formulation of claim 16, wherein the at least one water-soluble solubilizer is PEG-4000.

18. The solid solution capsule formulation of claim 17, wherein the total fill weight of said solid solution capsule is about 500 mg.

\* \* \* \* \*